United States Patent [19]

Beltz et al.

[11] Patent Number: 5,352,449
[45] Date of Patent: Oct. 4, 1994

[54] VACCINE COMPRISING RECOMBINANT FELINE LEUKEMIA ANTIGEN AND SAPONIN ADJUVANT

[75] Inventors: Gerald A. Beltz, Lexington; Dante J. Marciani, Hopkinton; Chung-Ho Hung; Charlotte A. Kensil, both of Milford, all of Mass.

[73] Assignee: Cambridge Biotech Corporation, Worcester, Mass.

[21] Appl. No.: 869,082

[22] Filed: Apr. 14, 1992

Related U.S. Application Data

[63] Continuation of Ser. No. 538,678, Jun. 15, 1990, abandoned, which is a continuation of Ser. No. 55,298, May 29, 1987, abandoned, which is a continuation-in-part of Ser. No. 868,585, May 30, 1986, abandoned.

[51] Int. Cl.⁵ .................... A61K 39/39; A61K 39/12
[52] U.S. Cl. ........................ 424/187.1; 424/207.1; 424/278.1; 424/819; 514/8; 514/12
[58] Field of Search ............... 424/89, 88, 91, 92; 514/12, 8; 530/350; 435/69.3

[56] References Cited

U.S. PATENT DOCUMENTS

| | | | |
|---|---|---|---|
| 3,969,907 | 6/1976 | Jarrett et al. | 424/89 |
| 4,034,081 | 7/1977 | Jarrett et al. | 424/89 |
| 4,086,134 | 4/1978 | Jarrett et al. | 195/1.2 |
| 4,117,112 | 9/1978 | Jarrett et al. | 424/89 |
| 4,264,587 | 4/1981 | Pedersen et al. | 424/89 |
| 4,332,793 | 6/1982 | Olson | 424/89 |
| 4,335,113 | 6/1982 | Combier et al. | |
| 4,406,885 | 9/1983 | Pinter | 424/89 |
| 4,434,157 | 2/1984 | Olsen | 424/89 |
| 4,663,436 | 5/1987 | Elder et al. | 424/88 |
| 4,669,785 | 10/1987 | Pedersen | 424/89 |
| 4,701,416 | 10/1987 | Nunberg | 530/808 |
| 4,789,702 | 12/1988 | Nunberg | 530/324 |
| 5,057,540 | 10/1991 | Kensil et al. | 514/25 |

FOREIGN PATENT DOCUMENTS

| | | |
|---|---|---|
| 0173997 | 9/1985 | European Pat. Off. |
| 0156299 | 10/1985 | European Pat. Off. |
| 0216564 | 9/1986 | European Pat. Off. |
| 2445338 | 7/1980 | France |
| 8502625 | 6/1985 | PCT Int'l Appl. |
| 8603224 | 6/1986 | PCT Int'l Appl. |
| 2038338 | 7/1980 | United Kingdom |

OTHER PUBLICATIONS

Collett (1989) Vaccine Biotechnology 33:109–172.
Marciani et al (1991) Vaccine 9:89–96.
Christensen (1990) Genetic Engineering News vol. 10, No. 8, Sep. issue.
Salerno et al (1978) J. Natl. Cancer Inst. 61(6):1487–1493.
Kensil et al (1991) J. Immunology 146(2):431–437.
Chem. Abs., vol. 90, 1979, 4333s.
Chem. Abs., vol. 72, 1970, 88330c.
Chem. Abs., vol. 98, 1983, 15205t.
Archiv. fur die gesamte virus forchung 44, 243–254 (1974), K. Dalsgaard.
Strouss et al, J. Virol., 61(11), pp. 3410–3415 (1987), [Chem. Abs. 108(15), 129718t].
Pinter, Gen. Offen., 14 pp., (1980), [Chem. Abs. 93(24), 225622z.].
Youngren et al, Cancer Res. vol. 44(8), pp. 3512–3517, (1984), [Chem. Abs. 101(13), 108693w].
Jarrett, O. et al., International J. Cancer 16:134 (1975).
Osterhaus, A. et al., J. Immunol. 135:591 (1985).
Pedersen, N. C. et al., Feline Practice 15:7 (1985).
Olsen, R. G. et al., Feline Practice 16:4 (1986).
Higuchi, R. et al., Phytochem. 26:229 (1987).
Higuchi, R. et al., Phytochem. 26:2357 (1987).
Dalsgaard, K., Arch. Gesamte Virusforschung 44:243 (1974); Chem. Abstr. 428:176074p (1974).
Elder, J. H. et al., J. Virol. 46:871 (1983).
Nunberg, J. H. et al., J. Virol. 49:629 (1984).
Pinter, A. et al., J. Virol. 49:452 (1984).
Nunberg, J. H. et al., PNAS 81:3675 (1984).
Nagasawa et al., Chem. Pharm. Bull. 28(7):2059–2064 (1980).
Stewart et al., J. Virology 58(3):825–834 (1986).

Primary Examiner—Kay K. Kim
Attorney, Agent, or Firm—Sterne, Kessler, Goldstein & Fox

[57] ABSTRACT

The invention relates to antigenic preparations useful for inducing the production of antibodies in a cat which will bind to epitopes on feline leukemia virus. Also disclosed are immunogenic compositions and methods for immunizing a cat to enable the production of antibodies to feline leukemia virus.

9 Claims, 28 Drawing Sheets

```
C TGC AGG ACC AAC CAC CAA TCA AGA CCT CTC GGA CAG CCC CAG CTC AGA CGA TCC ATC AAC                    61

ATG GAA AGT CCA ACG CAC CCA AAA CCC TCT AAA GAT AAG ACT CTC TCG TGG AAC TTA GTG                     121
Met Glu Ser Pro Thr His Pro Lys Pro Ser Lys Asp Lys Thr Leu Ser Trp Asn Leu Val

TTT CTG GTG GGG ATC TTA TTC ACA ATA GAC ATA GGA ATG GCC AAT CCT AGT CCA CAC CAA                     181
Phe Leu Val Gly Ile Leu Phe Thr Ile Asp Ile Gly Met Ala Asn Pro Ser Pro His Gln

ATA TAT AAT GTA ACT TGG GTA ATA ACC AAT GTA CAA ACT AAC ACC CAA GCT AAT GCC ACC                     241
Ile Tyr Asn Val Thr Trp Val Ile Thr Asn Val Gln Thr Asn Thr Gln Ala Asn Ala Thr

TCT ATG TTA GGA ACC TTA ACC GAT GCC TAC CCT ACC CTA CAT GTT GAC CTA TGT GAC CTA                     301
Ser Met Leu Gly Thr Leu Thr Asp Ala Tyr Pro Thr Leu His Val Asp Leu Cys Asp Leu

GTG GGA AAC ACC TGG GAA CCT ATA GTC CTA GAT CCA ACC AAT GTA AAA CAC GGG GCA CGT                     361
Val Gly Asn Thr Trp Glu Pro Ile Val Leu Asp Pro Thr Asn Val Lys His Gly Ala Arg
```

FIG.4A

```
421  TAC TCC TCC TCA AAG TAT GGA TGT AAA ACT ACA GAT AGA AAA AAA CAC CAA CAA ACA TAC
     Tyr Ser Ser Ser Lys Tyr Gly Cys Lys Thr Thr Asp Arg Lys Lys Gln Gln Gln Thr Tyr

481  CCC TTT TAC GTC TGC CCC GGA CAT GCC CCC TCG CTG GGG CCA AAG GGA ACA CAC TGT GGA
     Pro Phe Tyr Val Cys Pro Gly His Ala Pro Ser Leu Gly Pro Lys Gly Thr His Cys Gly

541  GGG GCA CAA GAT GGG TTT TGT GCC GCA TGG GGA TGT GAG ACC ACC GGA GAA GCT TGG TGG
     Gly Ala Gln Asp Gly Phe Cys Ala Ala Trp Gly Cys Glu Thr Thr Gly Glu Ala Trp Trp

601  AAG CCC TCC TCC TCA TGG GAC TAT ATC ACA GTA AAA AGA GGG AGT AGT CAG GAC AAT AGC
     Lys Pro Ser Ser Ser Trp Asp Tyr Ile Thr Val Lys Arg Gly Ser Ser Gln Asp Asn Ser

661  TGT GAG GGA AAA TGC AAC CCC CTG ATT TTC CAG TTC ACC CAG AAG GGA AGA CAA GCC TCT
     Cys Glu Gly Lys Cys Asn Pro Leu Ile Phe Gln Phe Thr Gln Lys Gly Arg Gln Ala Ser

721  TGG GAC GGA CCT AAG ATG TGG GGA TTG CGA CTA TAC CGT ACA GGA TAT GAC CCT ATC GCC
     Trp Asp Gly Pro Lys Met Trp Gly Leu Arg Leu Tyr Arg Thr Gly Tyr Asp Pro Ile Ala
```

FIG. 4B

```
TTA TTC ACG GTG TCC CGG CAG GTG TCA ACC ATT ACG CCG CCT CAG GCA ATG GGA CCC AAC    781
Leu Phe Thr Val Ser Arg Gln Val Ser Thr Ile Thr Pro Pro Gln Ala Met Gly Pro Asn

CTA GTC TTA CCT GAT CAA AAA CCC CCA TCC CGA CAA TCC CAA ACA GGG TCC AAA GTG GCG    841
Leu Val Leu Pro Asp Gln Lys Pro Pro Ser Arg Gln Ser Gln Thr Gly Ser Lys Val Ala

ACC CAG AGG CTC CAA ACG AAT GAA AGC GCC TCA AGG TCT GTT GCC CCC ACC GTG GTT        901
Thr Gln Arg Leu Gln Thr Asn Glu Ser Ala Ser Arg Ser Val Ala Pro Thr Val Val

CCC AAA CGG ATT GGG ACC GGA GAT AGG TTA ATA AAT TTA GTA CAA GGG ACA TAC CTA GCC    961
Pro Lys Arg Ile Gly Thr Gly Asp Arg Leu Ile Asn Leu Val Gln Gly Thr Tyr Leu Ala

TTA AAT GCC ACC GAC CCC AAC AAA ACT AAA GAC TGT TGG CTC TGC CTG GTT TCT CGA CCA    1021
Leu Asn Ala Thr Asp Pro Asn Lys Thr Lys Asp Cys Trp Leu Cys Leu Val Ser Arg Pro

CCC TAT TAC GAA GGG ATT GCA ATC TTA GGT AAC TAC AGC AAC CAA ACA AAC CCC CCA        1081
Pro Tyr Tyr Glu Gly Ile Ala Ile Leu Gly Asn Tyr Ser Asn Gln Thr Asn Pro Pro Pro
```

FIG.4C

```
TCC TGC CTA TCT ACT CCG CAA CAC AAA CTG ACC ATA TCT GAA GTA TCA GGG CAA GGA CTG    1141
Ser Cys Leu Ser Thr Pro Gln His Lys Leu Thr Ile Ser Glu Val Ser Gly Gln Gly Leu

TGC ATA GGG ACT GTT CCT AAG ACC CAC CAG GCT TTG TGC AAT GAG ACA CAA CAG GGA CAT    1201
Cys Ile Gly Thr Val Pro Lys Thr His Gln Ala Leu Cys Asn Glu Thr Gln Gln Gly His

ACA GGG GCG CAC TAT CTA GCC CCC CCC AAT GGC ACC TAT TGG GCC TGT AAC ACT GGA CTG    1261
Thr Gly Ala His Tyr Leu Ala Pro Pro Asn Gly Thr Tyr Trp Ala Cys Asn Thr Gly Leu

ACC CCA TGC ATT TCC ATG GCG CTG CTC AAT TGG ACC TCT GAT TTT TGT GTC TTA ATC GAA    1321
Thr Pro Cys Ile Ser Met Ala Val Leu Asn Trp Thr Ser Asp Phe Cys Val Leu Ile Glu

TTA TGG CCC AGA GTG ACT TAC CAT CAA CCC GAA TAT GTG TAC ACA CAT TTT GCC AAA GCT    1381
Leu Trp Pro Arg Val Thr Tyr His Gln Pro Glu Tyr Val Tyr Thr His Phe Ala Lys Ala

GTC AGG TTC CGA AGA GAA CCA ATA TCA CTA ACT GTT GCC CTC ATG TTG GGA GGA CTC ACT    1441
Val Arg Phe Arg Arg Glu Pro Ile Ser Leu Thr Val Ala Leu Met Leu Gly Gly Leu Thr
```

FIG.4D

```
GTA GGG GGC ATA GCC GCG GGG GTC GGA ACA GGG ACT AAA GCC CTC CTT GAA ACA GCC CAG    1501
Val Gly Gly Ile Ala Ala Gly Val Gly Thr Gly Thr Lys Ala Leu Leu Glu Thr Ala Gln

TTC AGA CAA CTA CAA ATG GCC ATG CAC ACA GAC ATC CAG GCC CTA GAA GAG TCA ATT AGT    1561
Phe Arg Gln Leu Gln Met Ala Met His Thr Asp Ile Gln Ala Leu Glu Glu Ser Ile Ser

GCC TTA GAA AAG TCC CTG ACC TCC CTT TCT GAA GTA GTC TTA CAA AAC AGA CGG GGC CTA    1621
Ala Leu Glu Lys Ser Leu Thr Ser Leu Ser Glu Val Val Leu Gln Asn Arg Arg Gly Leu

GAT ATT CTA TTC TTA CAA GAG GGA CTC TGT GCC GCA TTA AAA GAA GAA TGT TGC TTC        1681
Asp Ile Leu Phe Leu Gln Glu Gly Leu Cys Ala Ala Leu Lys Glu Glu Cys Cys Phe

TAT GCG GAT CAC ACC GGA CTC GTC CGA GAC AAT ATG GCT AAA TTA AGA GAA AGA CTA AAA    1741
Tyr Ala Asp His Thr Gly Leu Val Arg Asp Asn Met Ala Lys Leu Arg Glu Arg Leu Lys

CAG CGG CAA CAA CTA TTT GAC TCC CAA CAG GGA TGG TTT GAA GGA TGG TTC AAC AAG TCC    1801
Gln Arg Gln Gln Leu Phe Asp Ser Gln Gln Gly Trp Phe Glu Gly Trp Phe Asn Lys Ser
```

FIG. 4E

CCC TGG TTC ACA ACC CTA ATT TCC TCC ATT ATG GGC CCC TTA CTA ATC CTA CTC CTA ATT
Pro Trp Phe Thr Thr Leu Ile Ser Ser Ile Met Gly Pro Leu Leu Ile Leu Leu Ile        1861

CTC CTC TTC GGC CCA TGC ATC CTT AAC AGA TTA GTA CAA TTC GTA AAA GAC AGA ATA TCT
Leu Leu Phe Gly Pro Cys Ile Leu Asn Arg Leu Val Gln Phe Val Lys Asp Arg Ile Ser    1921

GTG GTA CAA GCC TTA ATT TTA ACC CAA CAG TAC CAA CAG ATA AAG CAA TAC GAT CCG GAC
Val Val Gln Ala Leu Ile Leu Thr Gln Gln Tyr Gln Gln Ile Lys Gln Tyr Asp Pro Asp    1981

CGA CCA TGA TTT CCA ATT AAA TGT ATG ATT CCA TTT AGT CCC CAG AAA AAG GGG GGA ATG
Arg Pro ———                                                                         2041

CTA CCC CAA AAT TTA GCC AGC TAC TGC AG                                              2084

FIG.4F

```
                       Vector Sequences                     | Linker    |  FEA-3281
                                                            | Sequences |  Nucleotide #162
                                                            |           |  |
ATG GTT CGT GCA AAC AAA CGC AAC GAG GCT CTA CGA ATC GCG | GAT CCC G |  CC AAT CCT AGT   786
Met Val Arg Ala Asn Lys Arg Asn Glu Ala Leu Arg Ile Ala | Asp Pro   | Ala Asn Pro Ser CCA CAC CAA ATA TAT AAT GTA ACT TGG GTA ATA ACC AAT GTA CAA ACT AAC ACC CAA GCT        846
Pro His Gln Ile Tyr Asn Val Thr Trp Val Ile Thr Asn Val Gln Thr Asn Thr Gln Ala AAT GCC ACC TCT ATG TTA GGA ACC TTA ACC GAT GCC TAC CCT ACC CTA CAT GTT GAC CTA        906
Asn Ala Thr Ser Met Leu Gly Thr Leu Thr Asp Ala Tyr Pro Thr Leu His Val Asp Leu TGT GAC CTA GTG GGA AAC ACC TGG GAA CCT ATA GTC CTA GAT CCA ACC AAT GTA AAA CAC        966
Cys Asp Leu Val Gly Asn Thr Trp Glu Pro Ile Val Leu Asp Pro Thr Asn Val Lys His
```

FIG.6A

```
GGG GCA CGT TAC TCC TCC TCA AAG TAT GGA TGT AAA ACT ACA GAT AGA AAA CAG CAA          1026
Gly Ala Arg Tyr Ser Ser Ser Lys Tyr Gly Cys Lys Thr Thr Asp Arg Lys Gln Gln

CAA ACA TAC CCC TTT TAC GTC TGC CCC GGA CAT GCC CCC TCG CTG GGG CCA AAG GGA ACA      1086
Gln Thr Tyr Pro Phe Tyr Val Cys Pro Gly His Ala Pro Ser Leu Gly Pro Lys Gly Thr

CAC TGT GGA GGG GCA CAA GAT GGG TTT TGT GCC GCA GCA TGG GGA TGT GAG ACC ACC GGA GAA  1146
His Cys Gly Gly Ala Gln Asp Gly Phe Cys Ala Ala Trp Gly Cys Glu Thr Thr Gly Glu

GCT TGG TGG AAG CCC TCC TCC TCA TGG GAC TAT ATC ACA GTA AAA AGA GGG AGT AGT CAG      1206
Ala Trp Trp Lys Pro Ser Ser Ser Trp Asp Tyr Ile Thr Val Lys Arg Gly Ser Ser Gln

GAC AAT AGC TGT GAG GGA AAA TGC AAC CCC CTG ATT TTG CAG TTC ACC CAG AAG GGA AGA      1266
Asp Asn Ser Cys Glu Gly Lys Cys Asn Pro Leu Ile Leu Gln Phe Thr Gln Lys Gly Arg

CAA GCC TCT TGG GAC GGA CCT AAG ATG TGG GGA TTG CGA CTA TAC CGT ACA GGA TAT GAC      1326
Gln Ala Ser Trp Asp Gly Pro Lys Met Trp Gly Leu Arg Leu Tyr Arg Thr Gly Tyr Asp
```

FIG. 6B

```
CCT ATC GCC TTA TTC ACG GTG TCC CGG CAG GTG TCA ACC ATT ACG CCG CCT CAG GCA ATG    1386
Pro Ile Ala Leu Phe Thr Val Ser Arg Gln Val Ser Thr Ile Thr Pro Pro Gln Ala Met

GGA CCC AAC CTA GTC TTA CCT GAT CAA AAA CCC CCA TCC CGA CAA ACA GGG TCC            1446
Gly Pro Asn Leu Val Leu Pro Asp Gln Lys Pro Pro Ser Arg Gln Thr Gly Ser

AAA GTG GCG ACC CAG AGG CTC CAA ACG AAT GAA AGC GCC TCA AGG TCT GTT GCC CCC ACC    1506
Lys Val Ala Thr Gln Arg Leu Gln Thr Asn Glu Ser Ala Ser Arg Ser Val Ala Pro Thr

ACC GTG GTT CCC AAA CGG ATT GGG ACC GGA GAT AGG TTA ATA AAT TTA GTA CAA GGG ACA    1566
Thr Val Val Pro Lys Arg Ile Gly Thr Gly Asp Arg Leu Ile Asn Leu Val Gln Gly Thr

TAC CTA GCC TTA AAT GCC ACC GAC CCC AAC AAA GAC TGT TGG CTC TGC CTG GTT            1626
Tyr Leu Ala Leu Asn Ala Thr Asp Pro Asn Lys Asp Cys Trp Leu Cys Leu Val

TCT CGA CCA CCC TAT TAC GAA GGG ATT GCA ATC TTA GGT AAC TAC AGC AAC CAA ACA AAC    1686
Ser Arg Pro Pro Tyr Tyr Glu Gly Ile Ala Ile Leu Gly Asn Tyr Ser Asn Gln Thr Asn
```

FIG.6C

```
CCC CCC CCA TCC TGC CTA TCT ACT CCG CAA CAC AAA CTG ACC ATA TCT GAA GTA TCA GGG     1746
Pro Pro Pro Ser Cys Leu Ser Thr Pro Gln His Lys Leu Thr Ile Ser Glu Val Ser Gly

CAA GGA CTG TGC ATA GGG ACT GTT CCT AAG ACC CAC CAG GCT TTG TGC AAT GAG ACA CAA     1806
Gln Gly Leu Cys Ile Gly Thr Val Pro Lys Thr His Gln Ala Leu Cys Asn Glu Thr Gln

CAG GGA CAT ACA GGG GCG CAC TAT CTA GCC GCC CCC AAT GGC ACC TAT TGG GCC TGT AAC     1866
Gln Gly His Thr Gly Ala His Tyr Leu Ala Ala Pro Asn Gly Thr Tyr Trp Ala Cys Asn

ACT GGA CTG ACC CCA TGC ATT TCC ATG GCG GTG CTC AAT GTG CTC AAT TGG ACC TCT GAT TTT TGT GTC     1926
Thr Gly Leu Thr Pro Cys Ile Ser Met Ala Val Leu Asn Trp Thr Ser Asp Phe Cys Val

TTA ATC GAA TTA TGG CCC AGA GTG ACT TAC CAT CAA CCC GAA TAT GTG TAC ACA CAT TTT     1986
Leu Ile Glu Leu Trp Pro Arg Val Thr Tyr His Gln Pro Glu Tyr Val Tyr Thr His Phe gp70 | p15E
GCC AAA GCT GTC AGG TTC CGA AGA | GAA CCA ATA TCA CTA ACT GTT GCC CTC ATG TTG GGA   2046
Ala Lys Ala Val Arg Phe Arg Arg | Glu Pro Ile Ser Leu Thr Val Ala Leu Met Leu Gly
```

FIG.6D

```
GGA CTC ACT GTA GGG GGC ATA GCC GCC GGG GTC GGA ACA GGG ACT AAA GCC CTC CTT GAA   2106
Gly Leu Thr Val Gly Gly Ile Ala Ala Gly Val Gly Thr Gly Thr Lys Ala Leu Leu Glu

FEA-3281 Nucleotide #1520 | Linker and Vector
                                                | Sequences
ACA GCC CAG TTC AGA CAA CTA CAA ATG G           |CG GGA TCC TAG  ---              2145
Thr Ala Gln Phe Arg Gln Leu Gln Met Ala         | Gly Ser
```

FIG.6E

```
ATG GTT CGT GCA AAC AAA CGC AAC GAG GCT CTA CGA ATC GCC GAT CCC GCC AAT CCT AGT    786
Met Val Arg Ala Asn Lys Arg Asn Glu Ala Leu Arg Ile Ala Asp Pro Ala Asn Pro Ser

CCA CAC CAA ATA TAT AAT GTA ACT TGG GTA ATA ACC AAT GTA CAA ACT AAC ACC CAA GCT    846
Pro His Gln Ile Tyr Asn Val Thr Trp Val Ile Thr Asn Val Gln Thr Asn Thr Gln Ala

AAT GCC ACC TCT ATG TTA GGA ACC TTA ACC GAT GCC TAC CCT ACC CTA CAT GTT GAC CTA    906
Asn Ala Thr Ser Met Leu Gly Thr Leu Thr Asp Ala Tyr Pro Thr Leu His Val Asp Leu

TGT GAC CTA GTG GGA AAC ACC TGG GAA CCT ATA GTC CTA GAT CCA ACC AAT GTA AAA CAC    966
Cys Asp Leu Val Gly Asn Thr Trp Glu Pro Ile Val Leu Asp Pro Thr Asn Val Lys His
```

FIG.7A

```
GGG GCA CGT TAC TCC TCC TCA AAG TAT GGA TGT AAA ACT ACA GAT AGA AAA CAG CAA      1026
Gly Ala Arg Tyr Ser Ser Ser Lys Tyr Gly Cys Lys Thr Thr Asp Arg Lys Gln Gln

CAA ACA TAC CCC TTT TAC GTC TGC CCC GGA CAT GCC CCC CTG GGG CCA AAG GGA ACA      1086
Gln Thr Tyr Pro Phe Tyr Val Cys Pro Gly His Ala Pro Leu Gly Pro Lys Gly Thr

CAC TGT GGA GGG GCA CAA GAT GGG TTT TGT GCC GCA TGG GGA TGT GAG ACC ACC GGA GAA  1146
His Cys Gly Gly Ala Gln Asp Gly Phe Cys Ala Ala Trp Gly Cys Glu Thr Thr Gly Glu

GCT TGG TGG AAG CCC TCC TCC TCA TGG GAC TAT ATC ACA GTA AAA AGA GGG AGT AGT CAG  1206
Ala Trp Trp Lys Pro Ser Ser Ser Trp Asp Tyr Ile Thr Val Lys Arg Gly Ser Ser Gln

GAC AAT AGC TGT GAG GGA AAA TGC AAC CCC CTG ATT TTG CAG TTC ACC CAG AAG GGA AGA  1266
Asp Asn Ser Cys Glu Gly Lys Cys Asn Pro Leu Ile Leu Gln Phe Thr Gln Lys Gly Arg

CAA GCC TCT TGG GAC GGA CCT AAG ATG TGG GGA TTG CGA CTA TAC CGT ACA GGA TAT GAC  1326
Gln Ala Ser Trp Asp Gly Pro Lys Met Trp Gly Leu Arg Leu Tyr Arg Thr Gly Tyr Asp
```

FIG.7B

```
CCT ATC GCC TTA TTC ACG GTG TCC CGG CAG GTG TCA ACC ATT ACG CCG CCT CAG GCA ATG    1386
Pro Ile Ala Leu Phe Thr Val Ser Arg Gln Val Ser Thr Ile Thr Pro Pro Gln Ala Met

GGA CCC AAC CTA GTC TTA CCT GAT CAA AAA CCC CCA TCC CGA CAA TCC CAA ACA GGG TCC    1446
Gly Pro Asn Leu Val Leu Pro Asp Gln Lys Pro Pro Ser Arg Gln Ser Gln Thr Gly Ser

AAA GTG GCG ACC CAG AGG CTC CAA ACG AAT GAA AGC GCC TCA AGG TCT GTT GCC CCC ACC    1506
Lys Val Ala Thr Gln Arg Leu Gln Thr Asn Glu Ser Ala Ser Arg Ser Val Ala Pro Thr

ACC GTG GTT CCC AAA CGG ATT GGG ACC GGA GAT AGG TTA ATA AAT TTA GTA CAA GGG ACA    1566
Thr Val Val Pro Lys Arg Ile Gly Thr Gly Asp Arg Leu Ile Asn Leu Val Gln Gly Thr

TAC CTA GCC TTA AAT GCC ACC GAC CCC AAC AAA ACT AAA GAC TGT TGG CTC TGC CTG GTT    1626
Tyr Leu Ala Leu Asn Ala Thr Asp Pro Asn Lys Thr Lys Asp Cys Trp Leu Cys Leu Val

TCT CGA CCA CCC TAT TAC GAA GGG ATT GCA ATC TTA GGT AAC TAC AGC AAC CAA ACA AAC    1686
Ser Arg Pro Pro Tyr Tyr Glu Gly Ile Ala Ile Leu Gly Asn Tyr Ser Asn Gln Thr Asn
```

FIG.7C

```
CCC CCC CCA TCC TGC CTA TCT ACT CCG CAA CAC AAA CTG ACC ATA TCT GAA GTA TCA GGG     1746
Pro Pro Pro Ser Cys Leu Ser Thr Pro Gln His Lys Leu Thr Ile Ser Glu Val Ser Gly

CAA GGA CTG TGC ATA GGG ACT GTT CCT AAG ACC CAC CAG GCT TTG TGC AAT GAG ACA CAA     1806
Gln Gly Leu Cys Ile Gly Thr Val Pro Lys Thr His Gln Ala Leu Cys Asn Glu Thr Gln

CAG GGA CAT ACA GGG GCG CAC TAT CTA GCC GCC CCC AAT GGC ACC TAT TGG GCC TGT AAC     1866
Gln Gly His Thr Gly Ala His Tyr Leu Ala Ala Pro Asn Gly Thr Tyr Trp Ala Cys Asn

ACT GGA CTG ACC CCA TGC ATT TCC ATG GCG GTG CTC AAT TGG ACC TCT GAT TTT TGT GTC     1926
Thr Gly Leu Thr Pro Cys Ile Ser Met Ala Val Leu Asn Trp Thr Ser Asp Phe Cys Val

TTA ATC GAA TTA TGC CCC AGA GTG ACT TAC CAT CAA CCC GAA TAT GTG TAC ACA CAT TTT     1986
Leu Ile Glu Leu Trp Pro Arg Val Thr Tyr His Gln Pro Glu Tyr Val Tyr Thr His Phe

GCC AAA GCT GTC AGG TTC CCA GAT CCT AGG TAA ——                                       2019
Ala Lys Ala Val Arg Phe Pro Asp Pro Arg
```

FIG.7D

|Vector Sequences|Linker Sequences|FEA-3281 Nucleotide #162| |
|---|---|---|---|
|ATG GTT CGT GCA AAC AAA CGC AAC GAG GCT CTA CGA ATC GCG<br>Met Val Arg Ala Asn Lys Arg Asn Glu Ala Leu Arg Ile Ala|GAT CCC G<br>Asp Pro|CC AAT CCT AGT<br>Ala Asn Pro Ser|786|
|CCA CAC CAA ATA TAT AAT GTA ACT TGG GTA ATA ACC AAT GTA CAA ACT AAC ACC CAA GCT<br>Pro His Gln Ile Tyr Asn Val Thr Trp Val Ile Thr Asn Val Gln Thr Asn Thr Gln Ala| | |846|
|AAT GCC ACC TCT ATG TTA GGA ACC TTA ACC GAT GCC TAC CCT ACC CTA CAT GTT GAC CTA<br>Asn Ala Thr Ser Met Leu Gly Thr Leu Thr Asp Ala Tyr Pro Thr Leu His Val Asp Leu| | |906|
|TGT GAC CTA GTC GGA AAC ACC TGG GAA CCT ATA GTC CTA GAT CCA ACC AAT GTA AAA CAC<br>Cys Asp Leu Val Gly Asn Thr Trp Glu Pro Ile Val Leu Asp Pro Thr Asn Val Lys His| | |966|

FIG.8A

```
GGG GCA CGT TAC TCC TCA AAG TAT GGA TGT AAA ACT ACA GAT AGA AAA CAG CAA                    1026
Gly Ala Arg Tyr Ser Ser Lys Tyr Gly Cys Lys Thr Thr Asp Arg Lys Gln Gln

CAA ACA TAC CCC TTT TAC GTC TGC CCC GGA CAT GCC CCC TCG CTG GGG CCA AAG GGA ACA            1086
Gln Thr Tyr Pro Phe Tyr Val Cys Pro Gly His Ala Pro Ser Leu Gly Pro Lys Gly Thr

CAC TGT GGA GGG GCA CAA GAT GGG TTT TGT GCC GCA TGG GGA TGT GAG ACC ACC GGA GAA            1146
His Cys Gly Gly Ala Gln Asp Gly Phe Cys Ala Ala Trp Gly Cys Glu Thr Thr Gly Glu

GCT TGG TGG AAG CCC TCC TCA TGG GAC TAT ATC ACA GTA AAA AGA GGG AGT AGT CAG                1206
Ala Trp Trp Lys Pro Ser Ser Trp Asp Tyr Ile Thr Val Lys Arg Gly Ser Ser Gln

GAC AAT AGC TGT GAG GGA AAA TGC AAC CCC CTG ATT TTG CAG TTC ACC CAG AAG GGA AGA            1266
Asp Asn Ser Cys Glu Gly Lys Cys Asn Pro Leu Ile Leu Gln Phe Thr Gln Lys Gly Arg

CAA GCC TCT TGG GAC GGA CCT AAG ATG TGG GGA TTG CGA CTA TAC CGT ACA GGA TAT GAC            1326
Gln Ala Ser Trp Asp Gly Pro Lys Met Trp Gly Leu Arg Leu Tyr Arg Thr Gly Tyr Asp
```

FIG. 8B

```
CCT ATC GCC TTA TTC ACG GTG TCC CGG CAG GTG TCA ACC ATT ACG CCG CCT CAG GCA ATG    1386
Pro Ile Ala Leu Phe Thr Val Ser Arg Gln Val Ser Thr Ile Thr Pro Pro Gln Ala Met

GGA CCC AAC CTA GTC TTA CCT GAT CAA AAA CCC CCA TCC CGA CAA ACA GGG TCC            1446
Gly Pro Asn Leu Val Leu Pro Asp Gln Lys Pro Pro Ser Arg Gln Thr Gly Ser

AAA GTG GCG ACC CAG AGG CTC CAA ACG AAT GAA AGC GCC TCA AGG TCT GTT GCC CCC ACC    1506
Lys Val Ala Thr Gln Arg Leu Gln Thr Asn Glu Ser Ala Ser Arg Ser Val Ala Pro Thr

ACC GTG GTT CCC AAA CGG ATT GGG ACC GGA GAT AGG TTA ATA AAT TTA GTA CAA GGG ACA    1566
Thr Val Val Pro Lys Arg Ile Gly Thr Gly Asp Arg Leu Ile Asn Leu Val Gln Gly Thr

TAC CTA GCC TTA AAT GCC ACC GAC CCC AAC AAA ACT AAA GAC TGT TGG CTC TGC CTG GTT    1626
Tyr Leu Ala Leu Asn Ala Thr Asp Pro Asn Lys Thr Lys Asp Cys Trp Leu Cys Leu Val

TCT CGA CCA CCC TAT TAC GAA GGG ATT GCA ATC TTA GGT AAC TAC AGC AAC CAA ACA AAC    1686
Ser Arg Pro Pro Tyr Tyr Glu Gly Ile Ala Ile Leu Gly Asn Tyr Ser Asn Gln Thr Asn
```

FIG. 8C

```
CCC CCC CCA TCC TGC CTA TCT ACT CCG CAA CAC AAA CTG ACC ATA TCT GAA GTA TCA GGG
Pro Pro Pro Ser Cys Leu Ser Thr Pro Gln His Lys Leu Thr Ile Ser Glu Val Ser Gly    1746

CAA GGA CTG TGC ATA GGG ACT GTT CCT AAG ACC CAC CAG GCT TTG TGC AAT GAG ACA CAA
Gln Gly Leu Cys Ile Gly Thr Val Pro Lys Thr His Gln Ala Leu Cys Asn Glu Thr Gln    1806

CAG GGA CAT ACA GGG GCC CAC TAT CTA GCC GCC CCC AAT GGC ACC TAT TGG GCC TGT AAC
Gln Gly His Thr Gly Ala His Tyr Leu Ala Ala Pro Asn Gly Thr Tyr Trp Ala Cys Asn    1866

ACT GGA CTG ACC CCA TGC ATT TCC ATG GCG GTG CTC AAT TGG ACC TCT GAT TTT TGT GTC
Thr Gly Leu Thr Pro Cys Ile Ser Met Ala Val Leu Asn Trp Thr Ser Asp Phe Cys Val    1926

TTA ATC GAA TTA TGG CCC AGA GTG ACT TAC CAT CAA CCC GAA TAT GTG TAC ACA CAT TTT
Leu Ile Glu Leu Trp Pro Arg Val Thr Tyr His Gln Pro Glu Tyr Val Tyr Thr His Phe    1986 gp70 | p15E
GCC AAA GCT GTC AGG TTC CGA AGA | GAA CCA ATA TCA CTA ACT GTT GCC CTC ATG TTG GGA
Ala Lys Ala Val Arg Phe Arg Arg | Glu Pro Ile Ser Leu Thr Val Ala Leu Met Leu Gly   2046
```

FIG.8D

```
GGA CTC ACT GTA GGG GGC ATA GCC GCG GGG GTC GGA ACA GGG ACT AAA GCC CTC CTT GAA    2106
Gly Leu Thr Val Gly Gly Ile Ala Ala Gly Val Gly Thr Gly Thr Lys Ala Leu Leu Glu

ACA GCC CAG TTC AGA CAA CTA CAA ATG GCC ATG CAC ACA GAC ATC CAG GCC CTA GAA GAG    2166
Thr Ala Gln Phe Arg Gln Leu Gln Met Ala Met His Thr Asp Ile Gln Ala Leu Glu Glu

TCA ATT AGT GCC TTA GAA AAG TCC CTG ACC TCC CTT TCT GAA GTA GTC TTA CAA AAC AGA    2226
Ser Ile Ser Ala Leu Glu Lys Ser Leu Thr Ser Leu Ser Glu Val Val Leu Gln Asn Arg

CGG GGC CTA GAT ATT CTA TTC TTA CAA GAG GGA CTC GTC TGT GCC GCA TTA AAA GAA GAA    2286
Arg Gly Leu Asp Ile Leu Phe Leu Gln Glu Gly Leu Val Cys Ala Ala Leu Lys Glu Glu

TGT TGC TTC TAT GCG GAT CAC ACC GGA CTC GTC CGA GAC AAT ATG GCT AAA TTA AGA GAA    2346
Cys Cys Phe Tyr Ala Asp His Thr Gly Leu Val Arg Asp Asn Met Ala Lys Leu Arg Glu

AGA CTA AAA CAG CGG CAA CAA CTA TTT GAC TCC CAA CAG GGA TGG TTT GAA GGA TGG TTC    2406
Arg Leu Lys Gln Arg Gln Gln Leu Phe Asp Ser Gln Gln Gly Trp Phe Glu Gly Trp Phe
```

FIG. 8E

```
AAC AAG TCC CCC TGG TTC ACA ACC CTA ATT TCC TCC ATT ATG GGC CCC TTA CTA ATC CTA      2466
Asn Lys Ser Pro Trp Phe Thr Thr Leu Ile Ser Ser Ile Met Gly Pro Leu Leu Ile Leu

CTC CTA ATT CTC CTC TTC GGC CCA TGC ATC CTT AAC AGA TTA GTA CAA TTC GTA AAA GAC      2526
Leu Leu Ile Leu Leu Phe Gly Pro Cys Ile Leu Asn Arg Leu Val Gln Phe Val Lys Asp

AGA ATA TCT GTG GTA CAA GCC TTA ATT TTA ACC CAA CAG TAC CAA CAG ATA AAG CAA TAC      2586
Arg Ile Ser Val Val Gln Ala Leu Ile Leu Thr Gln Gln Tyr Gln Gln Ile Lys Gln Tyr

FEA-3281
                          Nucleotide #1990
                          ─┼─
GAT CCG GAC CGA CCA TGA ───                                                          2604
Asp Pro Asp Arg Pro ───
```

FIG. 8F

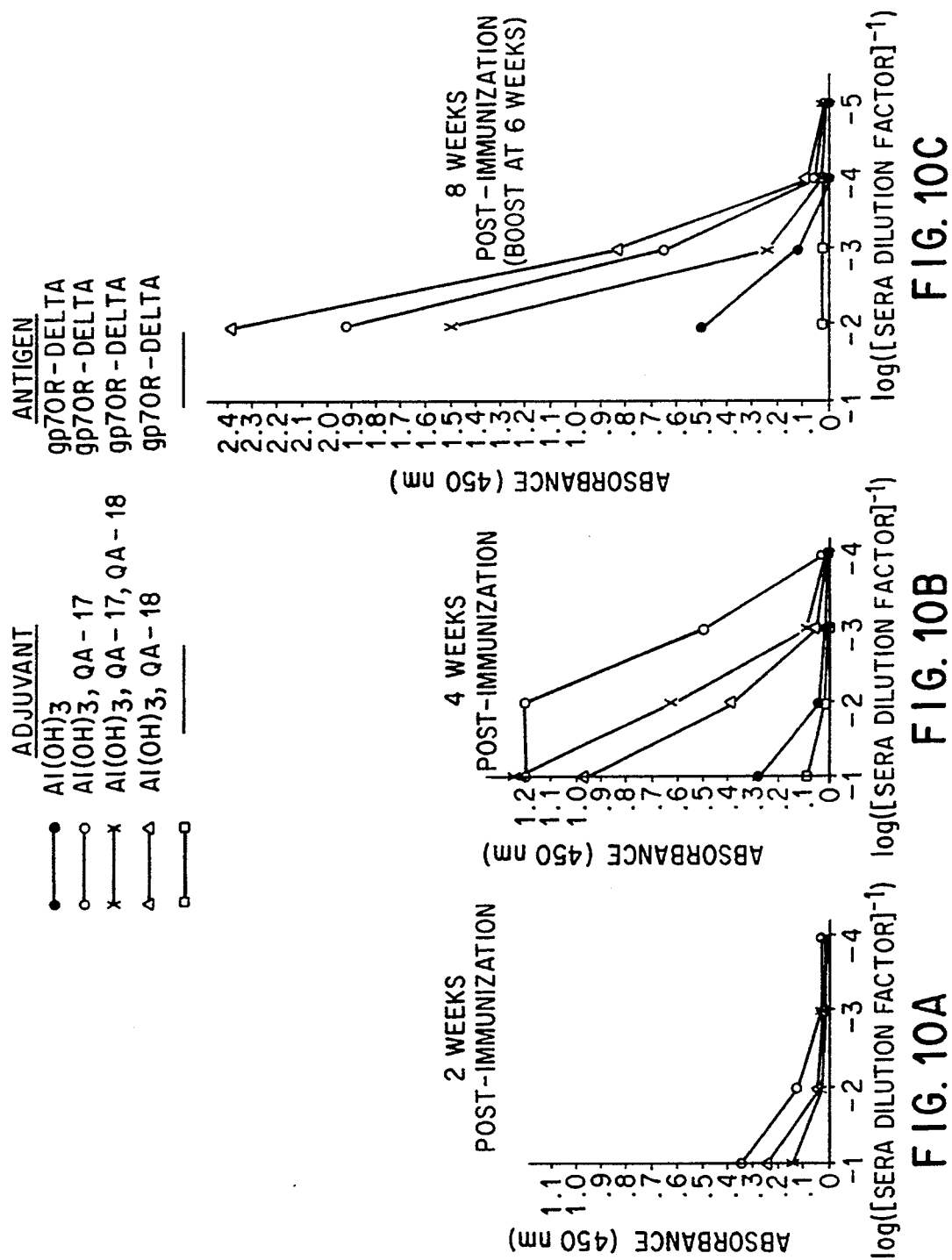

| ADJUVANT | ANTIGEN |
|---|---|
| ●——● Al(OH)$_3$ | ALKYLATED gp70R-DELTA |
| ○——○ Al(OH)$_3$, QA-17 | ALKYLATED gp70R-DELTA |
| ×——× Al(OH)$_3$, QA-18 | ALKYLATED gp70R-DELTA |
| △——△ Al(OH)$_3$, QA-7 | ALKYLATED gp70R-DELTA |
| □——□ Al(OH)$_3$, QA-17, QA-18 | ALKYLATED gp70R-DELTA |
| ▽——▽ Al(OH)$_3$, QA-7, QA-17 | ALKYLATED gp70R-DELTA |
| ■——■ Al(OH)$_3$, QA-7, QA-18 | ALKYLATED gp70R-DELTA |
| ▲——▲ | |

FIG. 11A — 2 WEEKS POST-IMMUNIZATION

FIG. 11B — 4 WEEKS POST-IMMUNIZATION

VACCINE COMPRISING RECOMBINANT FELINE LEUKEMIA ANTIGEN AND SAPONIN ADJUVANT

This application is a continuation of application Ser. No. 07/538,678, filed Jun. 15, 1990, now abandoned, which is a continuation of U.S. application Ser. No. 07/055,2398 filed May 29, 1987, now abandoned, which is a continuation-in-part application of U.S. application Ser. No. 06/868,585 filed May 30, 1986, now abandoned.

BACKGROUND OF THE INVENTION

1. Field of the Invention

The present invention relates to the use of feline leukemia virus (FeLV) antigens for inducing, in a cat, antibodies to FeLV.

2. Brief Description of the Background Art

Feline leukemia viruses (FeLV) are replication-competent type C retroviruses, which are epidemiologically associated with the horizontal transmission of leukemia, aplastic anemia, and acute immunosuppression (feline AIDS) in cats. The genome of FeLV consists of a 60–70S single-stranded RNA which consists of a gag gene encoding for viral core proteins, a pol gene coding for reverse transcriptase, and an env gene which encodes for the gp70 and p15E vital envelope proteins.

Isolates of FeLV may be divided into subgroups A, B, and C based upon their interference patterns (Sarma et al., *Virology* 44:352–358 (1971)). FeLV-A is found in all isolates, whereas FeLV-B occurs in about 40% of all isolates. FeLV-C is fairly rare and like FeLV-B is always found in combination with FeLV-A (Jarrett et al., *International Journal of Cancer* 21:334–337 (1978)). FeLV-C is found in only about 1% of all viremic cats and only in cats with anemia (Onions et al., *Nature* (London) 296:156–158 (1982)).

Numerous attempts to produce a vaccine against feline leukemia have been unsuccessful. These attempts include those containing virus killed by irradiation, hydroxylamine, or paraformaldehyde, and vaccines utilizing mitomycin D inactivated virus (U.S. Pat. Nos. Nos. 3,966,907, 4,034,081, and 4,086,134) or based on the use of whole live infected cells and inactivated infected cells.

More recently, interest has focused on the use of purified FeLV molecules (Osterhaus et al., *Journal of immunology* 135(1):591–596 (1985)) and on the use of a FOCMA (Feline Oncornavirus Associated Cell Membrane Antigen) preparation (U.S. Pat. Nos. 4,331,793 and 4,434,157). A vaccine utilizing a FOCMA preparation is commercially available (Norden Laboratories, Lincoln, Nebr.). However, a recent study of the efficacy of this vaccine casts serious doubt as to its ability to protect cats from FeLV disease (Pedersen et al., *Feline Practice* 15:7–20 (1985)). Thus, a considerable need exists for antigen preparations that can stimulate the cat immune system and induce antibodies to FeLV.

SUMMARY OF THE INVENTION

The present invention relates to antigenic preparations and methods of immunizing a cat to induce antibodies which react with epitopic determinants found on feline leukemia virus.

In the primary embodiment of the invention, an antigen preparation is produced which contains the polypeptide portion of the FeLV glycoprotein 70 (gp70) using recombinant DNA techniques. In another embodiment of the invention, an antigen preparation which contains the polypeptide portion of FeLV gp70 together with the 40 amino-terminal amino acids (termed "rgp70 delta") or with the entire amino acid sequence (termed "rgp90") of the p15e envelope protein of FeLV subgroup A is produced using recombinant DNA techniques. These recombinant polypeptides, gp70R, gp70R-delta, and gp90R, and analogs thereof, are hereinafter referred to collectively as gp70-containing protein(s). The term gp70-containing protein is intended to include polypeptides having the same amino acid sequence of the naturally occurring gp70 envelope protein, the gp70-delta protein, the gp90 protein and analogs thereof. The term "analogs" is intended to include proteins or polypeptides which differ from gp70, gp70-delta, or gp90 by addition, deletion or substitution of one or more amino acids providing that said polypeptide demonstrate substantially the biological activity of gp70 protein. These antigenic preparations can be used to immunize a cat such that antibodies are produced thereto.

Pharmaceutical compositions comprising the antigen preparation of the invention and immune response-enhancing components, together with pharmacologically appropriate carriers, are also included in this invention.

Thus, the invention comprises a substantially purified polypeptide comprising the amino acid sequence of the gp70-containing protein of feline leukemia virus, expression vehicles comprising a DNA sequence coding for said gp70-containing protein, prokaryotes transformed with said expression vehicle, methods of producing the gp70-containing protein in prokaryotes, and methods of inducing the production of antibodies in a cat to FeLV comprising immunizing said cat with a pharmaceutical composition comprising the recombinant gp70-containing protein from FeLV.

BRIEF DESCRIPTION OF THE FIGURES

FIGS. 4A–F show the vital DNA sequence and the corresponding amino acid sequence of gp70 and p15E.

FIGS. 6A–E show the DNA sequence present in, and corresponding amino acid sequence of, gp70R-delta as produced by, the expression vector pJLBOT.

FIGS. 7A–D show the DNA sequence present in, and corresponding amino acid sequence of gp70R as produced by, the expression vector pJLBOT.

FIGS. 8A–F show the DNA sequence present in, and corresponding amino acid sequence of gp90R as produced by, the expression vector pJLBOT.

FIGS. 10A–C show the results of immunization with gp70R-delta.

FIGS. 11A–B show the results of immunization with alkylated gp70R-delta.

BRIEF DESCRIPTION OF THE PREFERRED EMBODIMENTS

Figure 1:
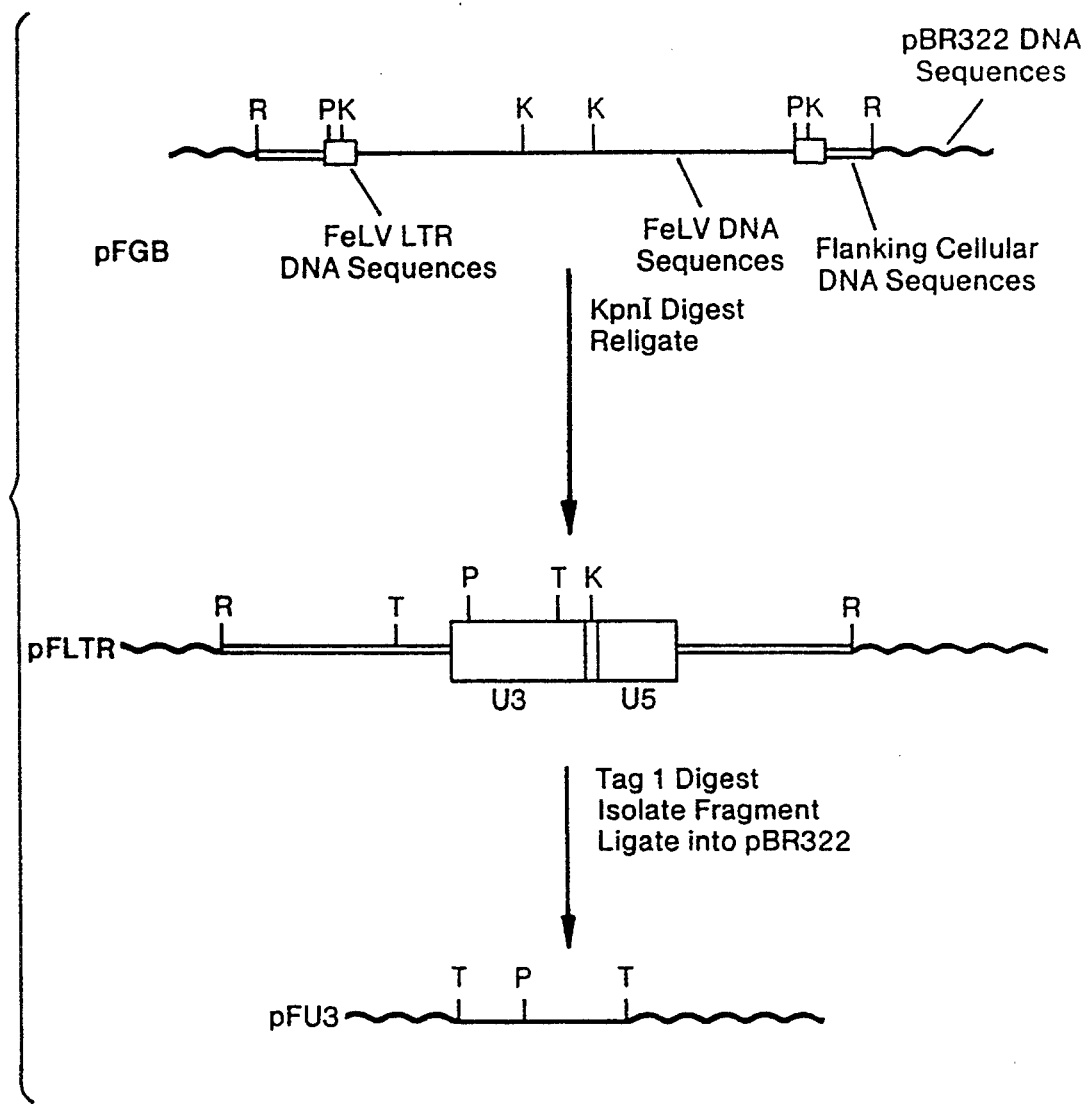
FIG. 1 outlines the construction of the pFU3 probe used to detect the presence of FeLV DNA sequences. Restriction endonuclease sites are located on the DNA as shown. R:Eco RI; P:Pst I; K:Kpn I; T:Taq I.

At its most fundamental levels, the invention comprises antigen preparations derived from feline leukemia virus and methods of utilizing these antigen preparations to stimulate the immune system of a cat and induce the production of antibodies to FeLV and immunologically related viruses.

The inventors have devised a method of producing the polypeptide portion of the gp70 glycoprotein of FeLV using recombinant DNA techniques. This was done by cloning the viral gene for gp70 into a plasmid vector which was then used to transform E. coli. When the vital gp70 genes are expressed in E. coli, the polypeptide which is produced is not glycosylated; hence, the molecular weight is approximately 45 Kd rather than 70 Kd. Thus, the viral protein produced in prokaryotes from the viral genes coding for gp70 is termed "gp70R" or "rec-gp70." In addition, when a gene coding for the FeLV viral gp70 envelope protein also encodes amino acids 1–40 of the p15e envelope protein of FeLV, the molecular weight of the polypeptide expressed in E. coli is 55 Kd. The viral protein produced in prokaryotes from the viral genes coding for gp70 and the 40 amino terminal amino acid residues of p15e polypeptide is termed "gp70R-delta" or "rec-gp70-delta." Additionally, the gene coding for the FeLV gp70 envelope and the complete p15e envelope protein encodes for a polypeptide which has a molecular weight of 65–70 Kd and is termed "rgp90," "gp90R," or "rec-gp90." These recombinant proteins are collectively termed "gp70 containing recombinant protein."

The term "immunologically related viruses" is meant to denote those viruses with significant genomic homology to FeLV such that the products expressed by these genes show significant levels of immunologic cross-reactivity. An example of such an immunologically related virus is feline sarcoma virus (FeSV).

FeSV is a retrovirus highly related to FeLV. In fact, FeSV can be isolated from tumors derived from FeLV-infected cats. In practice, FeSV is a defective virus which can only be propagated in the co-presence of FeLV as a helper virus. It is believed that, initially, the FeLV genome integrates into the feline DNA. However, during lytic transformation, when the retroviral DNA is removed from the feline DNA, it takes with it certain feline genes known as oncogenes. The resulting retrovirus, FeSV, is very similar to FeLV and is identical in terms of the envelope glycoproteins present on FeLV. In fact, preparations of FeSV isolated from infected cats also contain FeLV.

The term "host" as used in the present invention is meant to include not only prokaryotes but also such eukaryotes as yeasts and filamentous fungi as well as plant and animal cells.

The term "prokaryote" is meant to include all bacteria which can be transformed with the viral gene for the expression of the gp70 envelope protein of FeLV.

The viral genes for the gp70-containing protein can be derived from any subgroup of FeLV. All that is required is that the genetic sequence for the glycoprotein be expressed in the prokaryotic organism. Preferred is the viral gene for gp70-containing protein from FeLV subgroup A. Especially preferred is the viral gene for gp70 of FeLV subgroup A produced by cell line 3281. This cell line is available from the American Type Culture Collection, Rockville, Md., and has Accession No. CRL 9116.

A recombinant DNA molecule coding for the viral gp70-containing protein can be used to transform a host using any of the techniques commonly known to those of ordinary skill in the art. Especially preferred is the use of a plasmid containing the viral gp70 coding sequence for purposes of prokaryotic transformation.

The gp70-containing recombinant protein of the invention could have more or less amino acids at its flanking ends as compared to the amino acid sequence of native gp70. For example, the flanking amino acid sequence could include all or part of the p15E peptide as do the gp70R-delta and gp90R polypeptides. Alternatively, the recombinant protein of the invention could, for example, have two less arginine residues at the C-terminus, as shown in FIG. 7.

The term "substantially pure form" when applied to the polypeptide of the invention means that the polypeptide is essentially free of other vital proteins with which the polypeptide of the invention is normally associated in nature.

The term "substantially pure" when applied to saponins means substantially free from compounds normally associated with the saponin in its natural state and exhibiting constant and reproducible chromatographic response, elution profiles, and biologic activity. The term "substantially pure" is not meant to exclude artificial or synthetic mixtures of the saponin with other compounds.

Methods for preparing fused, operably linked genes and expressing them in bacteria are known and are shown, for example, in U.S. Pat. No. 4,366,246. The genetic constructs and methods described therein can be utilized for expression of gp70 from FeLV in prokaryotic hosts.

Prokaryotic hosts may include Gram negative as well as Gram positive bacteria, such as *E. coli, S. tymphimurium, Serratia marcescens,* and *Bacillus subtilis.*

In general, expression vectors containing promoter sequences which facilitate the efficient transcription of the inserted viral gene fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

Examples of promoters which can be used in the invention are: rec A, trp, lac, tac, and bacteriophage lambda $P_R$ or $P_L$. Examples of plasmids which can be used in the invention are listed in Maniatis et al., *Molecular Cloning,* Cold Spring Harbor Laboratories, 1982.

The invention extends to any host modified according to the methods described, or modified by any other methods, commonly known to those of ordinary skill in the art, such as, for example, by transfer of genetic material using a lysogenic phage, and which yield a prokaryote expressing the FeLV gene for gp70-containing protein.

Hosts, preferably prokaryotes, transformed with the FeLV viral genome for gp70-containing protein are particularly useful for the production of gp70R, gp70R-delta and gp90R polypeptide which can be used for the immunization of a cat. As stated previously, when the vital genome for gp70-containing protein is expressed in bacteria, glycosylation does not occur. Hence the recombinant gp70 has a molecular weight of 45 Kd rather than 70 Kd as when the genome is expressed by the virus.

The gp70R-delta comprises the entire amino acid sequence of the FeLV viral gp70 envelope protein and the 40 amino-terminal amino acid residues of the p15e envelope protein of FeLV subgroup A from cell line 3281. The p15e-derived sequence is located at the carboxyl terminus of the recombinant polypeptide. The molecular weight of the gp70R-delta polypeptide expressed in *E. coli* is 55 Kd. The vital protein produced in prokaryotes from the viral genes coding for gp70 and the p15e polypeptide (gp70R-delta) is more hydrophobic than gp70R due to the hydrophobic nature of the p15e-derived sequence. However, in both the naturally occurring (gp70) and recombinant (gp70R, gp70R-delta, and gp90R) forms, the amino acid sequence for the gp70 portion of the molecule is essentially the same. A cat immunized with gp70 recombinant protein will produce antibodies which will bind to epitopes present on the gp70R, gp70R-delta, gp90R and gp70 polypeptides. Thus, the commercial production of FeLV gp70-containing recombinant proteins can be carried out.

The term "immunogenically effective amount," as used in the invention, is meant to denote that amount of FeLV antigen which is necessary to induce the production in a cat of antibodies which will bind to FeLV epitopes.

The gp70-containing recombinant proteins of the invention is particularly useful in sensitizing the immune system of a cat such that, as one result thereof, antibodies reactive with epitopes present on FeLV are produced. Preferred are gp70R and gp70R-delta proteins derived from cell lines producing FeLV subgroup A. Especially preferred is the FeLV subgroup A-producing cell line 3281.

The gp70-containing recombinant proteins can be administered parenterally by injection, rapid infusion, nasopharyngeal absorption, dermal absorption, and orally. Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable forms for suspending the liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, and sweetening, flavoring, and perfuming agents.

It is also possible for the antigenic preparations containing the gp70-containing recombinant proteins of the invention to include an adjuvant. Adjuvants are substances that can be used to nonspecifically augment a specific immune response. Normally, the adjuvant and the antigen are mixed prior to presentation to the immune system, or presented separately, but into the same site of the animal being immunized. Adjuvants can be loosely divided into several groups based on their composition. These groups include oil adjuvants (for example, Freund's Complete and Incomplete), mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (for example, wax D from *Mycobacterium tuberculosis*, as well as substances found in *Corynebacterium parvum*, *Bordetella pertussis*, and members of the genus *Brucella*). Among those substances particularly useful as adjuvants are crude mixtures of saponins such as, for example, Quil A (Superlos A/S, Denmark) or highly purified fractions thereof.

The term "saponin" as used herein includes glycosidic triterpenoid compounds which produce foam in aqueous solution, have hemolytic activity, and posses immune adjuvant activity. The invention encompasses the saponin per se, as well as natural and pharmaceutically acceptable salts and pharmaceutically acceptable derivatives. The term "saponin" also encompasses biologically active fragments thereof.

Saponins are a mixture of triterpene glycosides extracted from the bark of the tree *Quillaja saponaria*. Saponins have been extensively employed as adjuvants in vaccines against foot and mouth disease, and in amplifying the protective immunity conferred by experimental vaccines against protozoal parasites such as *Trypanosoma cruzi* plasmodium and also the humeral response to sheep red blood cells (SRBC). (Bomford, *Int. Arch. Allerg. appl. immun.*, 67:127 (1982)). Recently, saponin adjuvants from Quil-A, a crude mixture of saponins, have been purified by high pressure liquid chromatography (HPLC). The purified fraction were prepared as described in copending U.S. patent application Ser. No. 07/573,268 filed Aug. 27, 1990, now U.S. Pat. No. 5,057,540 issued Oct. 15, 1991, which is a continuation of 07/200,754 filed May 31, 1988, now abandoned, which is a continuation-in-part of U.S. application Ser. No. 07/055,229, now abandoned, filed concurrently herewith, by Kensil et al. and entitled "Saponin Adjuvants," incorporated herein by reference. These purified fractions (substantially pure saponins), and mixtures thereof, are particularly useful in the present invention.

The physical form of the gp70-containing recombinant antigen which is used to immunize a cat can be either aggregated or non-aggregated. Studies thus far suggest that immunization with the aggregated form of gp70R in bacterial inclusions is most effective in ameliorating the deleterious effect of later exposure to vital infection. However, this finding does not preclude the production of aggregated gp70R from the non-aggregated form of gp70R by such common techniques as, for example, treatment with glutaraldehyde or other cross-linking agents. The aggregated gp70R thus derived could then be used for purposes of producing a vital infection-ameliorating composition effective in inducing an active immune reaction to protect against later exposure to FeLV or immunologically related viruses.

However, regardless of whether an animal is immunized with aggregated or non-aggregated gp70R, both of these forms of gp70R will cause the production of antibodies thereto. Thus, it is possible to use these anti-gp70R antibodies diagnostically as, for example, in a kit to detect the presence of gp70 in a specimen.

The FeLV antigen preparations of the invention can be used in a cat to induce the production of antibodies which will bind to epitopic determinants of FeLV. A particularly useful method in enhancing the production of cat antibodies to FeLV is to first immunize a cat with the FeLV antigenic preparation of the invention followed by a later immunization.

Although the age of the cat at the time of initial immunization is not critical, it is most preferable that the animal be at least eight weeks of age, since typically cats are weaned at approximately four weeks, and by waiting until eight weeks of age, interference due to circulating maternal antibody will have decreased.

One way of determining when a cat can most advantageously be immunized is by determining the cat's immune status with respect to gp70. This evaluation can be done by using the gp70-containing recombinant proteins of the invention in an immunoassay such as, for example, an ELISA assay to detect cat antibodies to gp70R. In so doing, it is possible to determine when the cat's antibody titer to gp70R is sufficiently low to enhance immunization and protect against infection by FeLV and immunologically related viruses.

Many different techniques exist for the timing of the immunizations when a multiple immunization regimen is utilized. It is possible to use the antigenic preparation of the invention more than once to increase the levels and diversity of expression of the immunoglobulin repertoire expressed by the immunized cat. Typically, if multiple immunizations are given, they will be spaced one to two months apart.

Generally, the dosage of gp70-containing recombinant protein administered to a cat will vary depending on such factors as age, condition, sex, and extent of disease, if any, and other variables which can be adjusted by one of ordinary skill in the art.

The antigenic preparations of the invention can be administered as either single or multiple dosages and can vary from 10–1,000 ug/ml for the FeLV gp70R or gp70R-delta antigen per dose, more preferably 100–700 ug/ml gp70R or gp70R-delta antigen per dose, most preferably 100–300 ug/ml gp70R or gp70R-delta antigen per dose. Similar dosage levels for gp70-containing recombinant protein are contemplated.

Having now generally described the invention, a more complete understanding can be obtained by reference to the following specific examples. These examples are provided for purposes of illustration only and are not intended to be limiting unless otherwise specified.

EXAMPLE 1

Isolation of a Subgroup a Genomic Clone

High molecular weight genomic DNA was prepared from 3281 cells, restricted to completion with endonuclease Eco RI, and 8–20 kilobase (kb) fragments isolated on a sucrose gradient. A lambda phage library was prepared from these fragments using Charon 4A Eco RI arms. This library was screened with a probe containing the U3 region of the Gardner-Arnstein FeLV subgroup B genomic clone as described by Mullins et al., *Journal of Virology* 38:688–703, 1981. DNA hybridizations using this region of the FeLV long terminal repeat (LTR) have been shown to be specific for horizontally transmitted FeLV DNA sequences (Casey et al., *Proceedings of the National Academy of Sciences, U.S.A.* 78:7778 (1981)). This exogenous U3 probe does not cross-hybridize with endogenous FeLV sequences found in DNA from uninfected cat cells. Construction of the U3 probe is outlined in FIG. 1.

Briefly, plasmid pFGB was constructed by subcloning a 9.1 kb Eco RI fragment from the FeLV DNA containing genomic clone lambda-HF60 (Mullins et al., supra.) into pBR322. This plasmid contains 4 Kpn I sites, two in the internal regions in the viral genome and one in the region of each long terminal repeat (LTR). Digestion of pFGB with Kpn I followed by religation results in a clone (pFLTR) containing flanking cellular genetic sequences and one LTR, but no other viral sequences. Next, pFLTR was digested with endonuclease Taq I and a 550 bp fragment was isolated. This fragment was then subcloned into the Cla I restriction site of pBR322. This clone, pFU3, was nick-translated directly and used as the hybridization probe.

Selection of recombinant phage was done based upon DNA hybridization to the radioactive nick-translated pFU3 probe. In this manner, 42 recombinant phage were selected and isolated and their DNA prepared. These genomic clones were restriction digested and analyzed by Southern hybridization using the pFU3 probe, an FeLV envelope probe (pFGB-env) from the Gardner-Arnstein molecular clone, and an additional probe (pFGB) containing the entire FeLV Garnder-Arnstein genome. Based upon this analysis, 28 distinct clones were identified. Of these 28 clones, 24 were found to be defective due to a major deletion in the gag/pol gene regions. The remaining four clones did not have this deletion and appeared to be full length.

Figure 2:
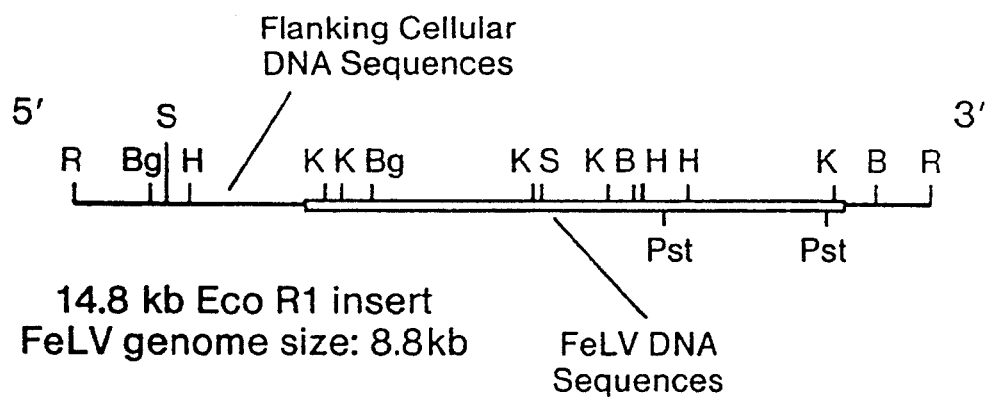
FIG. 2 shows the restriction map for clone 32–50. Restriction endonuclease sites are located on the DNA as shown. R:Eco RI; Bg:Bgl II; S:Sac I; H:Hind III; K:Kpn I; B:Bam HI.
Figure 3:
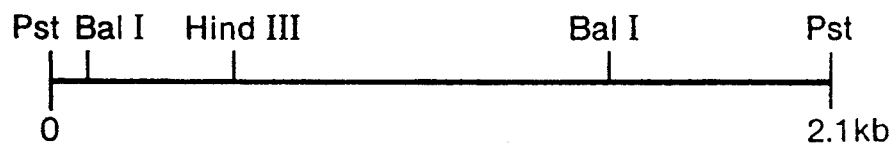
FIG. 3 shows the limited restriction map for the FeLV envelope gene subcloned into PUC-9.

One full-length clone (32–50), the restriction map for which is shown in FIG. 2, was chosen for further analysis. A 2.0 kb Pst I fragment containing the FeLV envelope gene was subcloned into PUC-9 and a limited restriction map determined (FIG. 3). Various fragments were further subcloned into M13 and the DNA sequences determined (also shown in FIG. 4).

EXAMPLE 2

Expression in *E. Coli* of FeLV gp70 and gp70-Delta

Figure 5:
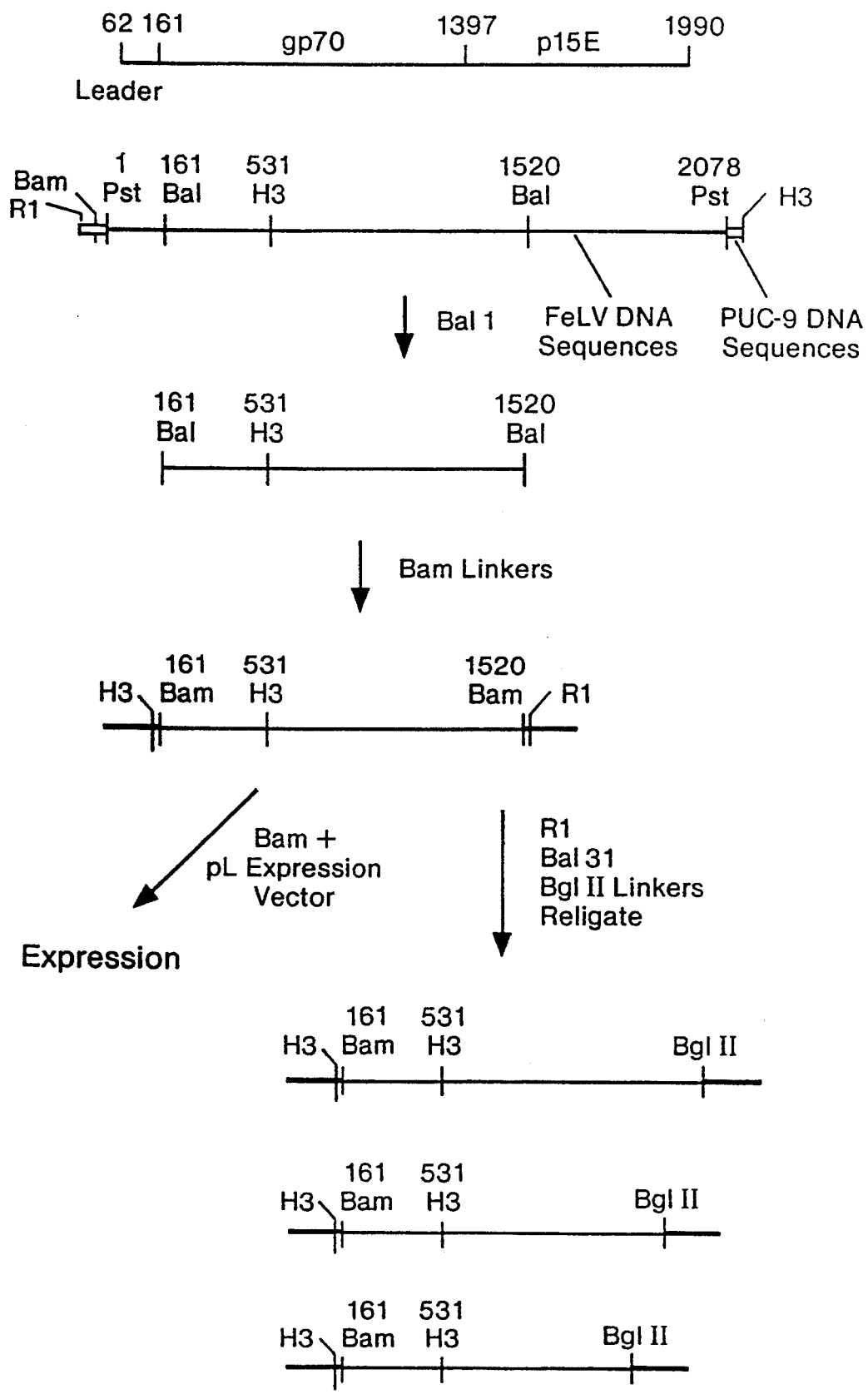
FIG. 5 shows the subcloning of the gp70-p15E fragment to obtain expression of the gp70 viral genes in producing gp70R.

There are two Bal I restriction sites in the envelope gene of the FeLV subgroup A genomic clone 32–50. One of these sites is located at nucleotide 161 (FIG. 4), which is very close to the junction between the leader sequence and the sequence encoding the amino end of the native gp70. The other restriction site is approximately 120 nucleotides beyond the gp70/p15E junction. The Bal I fragment was isolated, Bam HI linkers were added, and the modified fragment cloned into the Bam HI site of PUC-9 (penv-1) as shown in FIG. 5. This Bam HI fragment was also subcloned into the $P_{L'}$-based expression vector, pJLBOT, the resulting subclone of which is called R16–38, and protein expression induced. This 55 Kd protein is termed "gp70R-delta" and is also known as "rec-gp70-delta" or "rgp70-delta." The complete DNA sequence and the corresponding amino acid sequence is shown in FIG. 6.

*E. coli* strain R16–38, containing the vital genomic sequence for gp70-delta in plasmid pJLBOT, was deposited on May 22, 1987, at the American Type Culture Collection, Rockville, Md., and given Accession No. ATCC 67411.

The construction of expression plasmid pJLBOT originated by modifying plasmid PJLA16. The construction of the plasmid pJLA16 is described in Lautenberger et al., *Gene Anal. Tech.* 1:63–66 (1984). The pJLA16 plasmid contains the bacteriophage lambda $P_L$ promoter ($P_L$), and the Shine-Dalgarno sequence and leader sequence from the bacteriophage lambda $C_{II}$ gene. Initially, the expression plasmid pJLBO was prepared by digestion of pJLA16 with the restriction endonuclease Nru I. After digestion, a Bam HI linker was ligated to the cut plasmid. This process places a Bam HI restriction site at the end of the $C_{II}$ bacterial leader in the translation reading frame appropriate for expression of gp70R. Next, a synthetic oligonucleotide, containing translation terminators in all three reading frames, was cloned into plasmid pBR322 which was then shuttled into pJLBO behind the Bam HI cloning site. The resulting plasmid was designated pJLBOT.

Western blot analysis of the total protein extracts from induced cultures using a high titer rabbit antisera to gp70 indicated that an FeLV protein of approximately 55 Kd was present. This protein contains nearly all of the gp70 and 40 amino acids of p15E.

To generate clones that produce gp70 sequences without those derived from p15E, penv-1 was first linearized with Eco RI. Approximately 100 bp were removed from each end with Bal 31 exonucleoase, Bgl II linkers were added, and the DNA fragments recircularized with DNA ligase. Recombinant clones were selected and the extent of nuclease digestion and position of the Bgl II linkers within the FeLV 32-50 envelope gene was determined by DNA sequencing using the M-13/Sanger dideoxy method and a commercially available kit (Amersham). Clone pUC-R16-12 was found to have FeLV sequences that terminate within five nucleotides of the 3'-end of the gp70 coding region. The location of this 3'-end is shown in FIG. 4.

The Bam HI/Bgl II fragment from pUC-R6-12 was isolated and subcloned into the pL expression vector pJLBOT. Upon induction, a protein of approximately 45 Kd was produced that reacted with antisera to gp70. The complete amino acid sequence of this protein is shown in FIG. 7. The resulting clone was named R16-12.

*E. coli* strain R16-12, containing the vital genomic sequence for gp70 in plasmid pJLBOT, was deposited on May 22, 1986, at the American Type Culture Collection, Rockville, Md., and given Accession No. 67119.

EXAMPLE 3

Expression of FELV GP90 in *E. coli*

A recombinant DNA clone expressing FeLV gp90 was constructed beginning with plasmid FEA-3281. FEA-3281 was constructed by subcloning the 2 kb PstI fragment from genomic clone 32-50 into PUC-9 and contains the coding sequences for the FeLV envelope gene. A restriction map for FEA-3281 is presented in FIG. 3, and the sequence of the Felv derived portion of the plasmid is presented in FIG. 4. FEA-3281 was also used as the starting material for the generation of plasmids expressing gp70R and gp70R-delta.

FEA-3281 was restricted with HindIII to generate two DNA fragments of 3.3 and 5.5 kb. The 3.3 kb fragment was isolated and recircularized using T4 DNA ligase. The resulting plasmid was named FEA-env-5'.

FEA-env-5' was restricted with Bali. BamHI linkers were added and the plasmid recircularized. This plasmid was named FEA-env-5'-BH.

FEA-env-5'-BH was restricted with HindIII, and the 1.5 kb HindIII fragment generated from FEA-3281 was subcloned into this site in the original orientation. This plasmid was named ENV-L-.

ENV-L- was restricted with PstI and digested briefly with Bal 31 exonuclease. BglII linkers were added and the plasmid recircularized. The resulting plasmid was named PUC-gp90. The location of the BglII site in the FeLV envelope gene was determined by DNA sequencing.

The 2.0 kb BamHI/BglII fragment from PUC-gp90 was isolated and subcloned into the BamHI site of pLCBC00. pLCBC00 is identical to pJLBOT with the exception that pLCBC00 contains a PvuII restriction site between the DNA sequences originating from bacteriophage lambda pL and bacteriophage cII. This plasmid was named pCBC00gp90. Expression was induced in an identical fashion to that for gp70R and gp70R-delta. A 65-70 kd protein reactive with rabbit anti-gp70 antisera was produced upon induction. This protein was named gp90R. The complete DNA sequence encoding gp90R and corresponding amino acid sequence is presented in FIG. 8.

*E. coli* strain R16-12, containing the vital genomic sequence for gp90 in plasmid pLCBC00, was deposited on May 28, 1987, at the American Type Culture Collection, Rockville, Md., and given Accession No. 67412.

EXAMPLE 4

Purification of FeLV Recombinant gp70

Recombinant *E. coli* clone R16-12 was grown in LB medium supplemented with 1% glucose and 0.1% casamino acids at 32° C. to an optical density (560 nm) of 0.4-0.6. The culture was then shifted to 42° C. and incubated for an additional 2 hours. At the end of this time the cells were collected by centrifugation at 4,000 g for 30 minutes, washed with 50 mM Tris HCl, pH 7.5, containing 50 mM EDTA and 50 mM NaCl, and lysed by enzymatic digestion with lysozyme (5 Mg/g of cells) in 25 mM Tris HCl, pH 7.5, containing 0.5% Triton X-100. The cell lysate, was then fractionated by sedimentation for 30 minutes at 30,000 g. The cell pellet was resuspended in 50 mM Tris HCl, pH 7.5, containing 50 mM $MgCl_2$ and DNase I (0.1 Mg/g cells). After incubation at room temperature for 30 minutes with occasional stirring, the suspension was centrifuged at 6,000 g for 30 minutes and the pellet washed twice with 25 mM Tris HCl, pH 7.5, containing 0.5 M NaCl, 0.5% Triton X100, 25 mM EDTA, and 1% beta-mercaptoethanol. This treatment was followed by two washes with 4M urea in 25 mM Tris HCl, pH 7.5, containing 0.5M NaCl and 25 mM EDTA. The pellet resulting from this procedure contained more than 90% of the recombinant protein expressed in E. coli R16-12. Analysis by gel electrophoresis showed that the gp70R protein partially purified and present in bacterial inclusion bodies in aggregated form. This material is composed of 60-80% gp70R protein with the remainder of the material present as bacterial proteins. This material was designated Preparation I.

A second preparation of gp70R (Preparation II) was developed starting with Preparation I. The recombinant protein pellet of Preparation I was solubilized by resuspending the washed pellet in 50 mM Tris HCl, pH 9.0, in the presence of 6M urea and 1% beta-mercaptoethanol. The suspension was clarified by centrifugation at $10^5$ g for 30 Minutes.

To purify gp70R Preparation II, the supernatant following centrifugation was applied onto a Sepharose CL-4B column equilibrated with 50 mM Tris HCl, pH 9.0, containing 6M Urea and 1 mM beta-mercaptoethanol. The column was eluted with the same buffer at room temperature. Fractions were collected and examined by SDS-gel electrophoresis for the presence of gp70R. The fractions containing antigen were pooled and dialyzed against a series of buffers at 4° C.: first, 10 volumes of 50 mM Tris HCl, pH 7.7, containing 4M urea; second, 10 volumes of buffer containing 2M urea; third, 10 volumes of buffer containing 1M urea; and fourth, 100 volumes of buffer without urea. At the completion of dialysis, about 50% of the gp70R remained soluble in 50 mM Tris HCl, pH 7.5. Unlike the gp70R in Preparation I, the gp70R of Preparation II was found not to exist in aggregated form.

The aggregated form of gp70R present in Preparation I as well as the soluble, non-aggregated gp70R of Preparation II were used in cats to produce antibody to FeLV.

EXAMPLE 5

Purification of FeLV Recombinant GP70R-Delta

Inclusion Body Preparation

Recombinant *E. coli* clone R16-38 was grown in LB medium supplemented with 1% glucose and 0.1% casamino acids at 32° C. to an optical density (560 nm) of 0.4–0.6. The culture was then shifted to 42° C. and incubated for an additional 2 hours. At the end of this time the cells were collected by centrifugation at 4,000 g for 30 minutes, washed with 50 mM Tris HCl, pH 7.5, and finally resuspended in 200 ml 50 mM Tris HCl to which is added 1 ml 0.1M phenylmethylsulfonylfluoride in isopropanol (final concentration=0.5 mM) and 0.4 ml of 5 Mg/ml aprotinin (final concentration=10.0 ug/ml). The cells were lysed by enzymatic digestion with lysozyme (final concentration=0.5 Mg/ml) in the presence of 0.2% Triton X-100. After stirring for 30 minutes, 2 ml $MgCl_2$ (0.5M), 5 ml DNaseI (1 mg/ml) and 1 ml 0.1M phenylmethylsulfonylfluoride were added. After stirring for 30 additional minutes, 40 ml EDTA (0.25M, pH 7.5) and 4 ml Triton X-100 (10% w/v) were added. The preparation was centrifuged at 10,000×g for 30 minutes at 4° C., and the pellet was resuspended in 50 ml 50 mM Tris HCl pH 7.5. The pellet was homogenized at low speed for 15 seconds. Lysozyme was added to a concentration of 0.5 mg/ml and 0.6 ml of 10% Triton X-100 were added. After stirring for 15 minutes, 10 ml of $MgCl_2$ (0.5M) and 1 ml DNase I (1 mg/ml) were added and stirring was continued for an additional 15 minutes. After adjusting the volume to 300 ml with 50 mM Tris, pH 9.0, 40 ml of 10% Triton X-100 and 51.2 ml of EDTA (0.25M, pH 7.5) were added and the final volume adjusted to 400 ml with 50 mM Tris, pH 9.0. After stirring for 30 minutes, the suspension was centrifuged at 10,000×g for 30 minutes at 4° C., and the pellet was resuspended in 400 ml 50 mM Tris HCl pH 7.5, containing 4M urea, 50 mM EDTA, and 1% Triton X-100. After stirring for 15 minutes, the suspension was centrifuged at 10,000×g for 30 minutes at 4° C., and the pellet was resuspended in 400 ml 50 mM Tris HCl pH 7.5, containing 1.0M NaCl. After stirring for 15 minutes, the suspension was centrifuged at 10,000×g for 30 minutes at 4° C., and the pellet was resuspended in 400 ml 50 mM Tris HCl pH 7.5, containing 6M urea, and 5 mM EDTA. After stirring for 15 minutes, the suspension was centrifuged at 10,000×g for 30 minutes at 4° C. At this point the pellet of inclusion bodies was either frozen for future use or solubilized in 50 mM Tris HCl pH 9.5, containing 6M quanidine HCl, 50 mM EDTA, and 0.5% beta-mercaptoethanol. The gp70R-delta polypeptide was then purified by either of the methods of Example 6, below.

EXAMPLE 6

Purification of FeLV Recombinant Gp70R-Delta

Procedure I

The solubilized protein of Example 5 was dialyzed against 6M urea, 50 mM Tris-Cl, pH 8.0, 5 mM EDTA, and 1 mM dithiothreitol (DTT). Approximately 120 mg of the protein was applied to a CM-TSK column (EM Science, 1.5 cm ID×4 cm) equilibrated with the same buffer. The protein was eluted with a linear gradient of NaCl (0–1.0M in 150 ml) in the same buffer. The fractions were collected and analyzed by electrophoresis on 10% SDS-polyacrylamide gels. Coomassie blue-staining of the gel was used to identify the gp70R-delta protein. Fractions 25–31, eluting at approximately 0.1M NaCl, were pooled and used for immunization.

Procedure II

In order to decrease the hydrophobicity of gp70R-delta, the sulfhydryl groups were alkylated with iodoacetamide and the lysine residues were N-acylated with citraconic anhydride. The protein prepared as in Example 5 was solubilized in 6M quanidine-HCl in 50 mM borate, pH 9.0, 0.5% beta-mercaptoethanol (v/v). Iodoacetamide is added at a molar ratio of 1:1 (iodoacetamide:total sulfhydryl groups). The alkylation was carried out in the dark for 1 hour at room temperature. The alkylation of all sulfhydryl groups (in the protein and beta-mercaptoethanol) was monitored with DTNB (Ellman's reagent) to ensure complete alkylation. The protein concentration was adjusted to 2 mg/ml.

The protein was citraconylated in the dark by the addition of citraconic anhydride (0.0022 ml per mg protein; approximately 50 Molar excess over free lysines). The preparation was dialyzed several times in the dark against 50 mM borate, pH 9.0. The completion of the acylation of the protein lysine groups was determined by reaction with trinitrobenzene sulfonic acid (TNBS) which measures residual free lysine groups. TNBS (200 ul of 10 mM) was added to 200 ug alkylated, citraconylated, dialyzed gp70R-delta in 1 ml 50 mM sodium borate, pH 9.0. The mixture was incubated for 2 hours in the dark at 40° C., the reaction quenched with 0.5 ml of 1 N HCl and 0.5 ml of 1% SDS, and the absorbance was read at 340 nm. The molar extinction coefficient at 340 nm for TNP-lysine is 10,400.

The purification of the alkylated, citraconylated gp70R-delta was performed at pH 9.0 to prevent deblocking of lysine groups. Urea at a final concentration of 4M was added to the modified protein. The protein was concentrated to 3 mg/ml by ultrafiltration and applied to a Sepharose 6B-Cl column (1.5×86 cm). The gp70R-delta protein was eluted at a flow rate of 6.6 ml/hr with 4M urea, 50 mM sodium borate, pH 9.0. Fractions (5.3 ml/fraction) were collected and the gp70R-delta was determined by protein assay and SDS-polyacrylamide electrophoresis to be in fractions 13–15.

The citraconylation of gp70R-delta was reversed by dialyzing 5 ml of alkylated, citraconylated gp70R-delta (1.0 mg/ml) against 6M urea in 50 mM sodium citrate, pH 5.5 for 48 hours at room temperature. The gp70R-delta was dialyzed against 6M urea in 100 mM sodium bicarbonate, pH 8.0 and the protein concentration adjusted to 0.8 mg/ml prior to absorption to aluminum hydroxide.

Procedure III

A modification of the above purification of alkylated, citraconylated gp70R-delta was developed. Briefly, alkylated, citraconylated gp70R-delta is modified and dialyzed against 50 mM sodium borate, pH 9.0 as described above. Urea was added to a final concentration of 8.0M. The protein was concentrated by ultrafiltration with a PM-30Membrane to yield 2.5 mg protein/ml. The protein solution was applied to a Sephacryl S-400 column (1.5×90 cm) in a 50 mM sodium borate buffer, pH 9.0 containing 8M urea and eluted with the same buffer. Fractions (2.9 ml/fraction) were collected and fractions 34-37 containing gp70R-delta were pooled. Twenty one mg of the protein from these fractions were diluted to a final concentration of 4M urea with 50 mM sodium borate, pH 9.0 and applied to a DEAE-TSK column (1.5×11 cm). The protein was eluted with a linear gradient of NaCl (0-0.5M) in 50 mM sodium borate, pH 9.0 containing 4M urea. Three ml fractions were collected. Fractions 89-95 containing gp70R-delta were pooled and 15 mg of gp70R-delta was recovered.

EXAMPLE 7

Preparation of Purified Saponins

Briefly, aqueous extracts of the *Quillaja saponaria molina* bark were dialyzed against water. The dialyzed extract was extracted with methanol and the methanol-soluble extract was further fractionated on silica gel chromotography and by reverse phase high pressure liquid chromatography (RP-HPLC). The individual saponins were separated by reverse phase HPLC. At least 22 peaks detectable by refractive index (denominated QA-1 to QA-22) were separable. Each peak corresponded to a carbohydrate peak and exhibited only a single band on reverse phase thin layer chromatography. The individual components were identified by retention time on a Vydac C4 HPLC column as follows:

| Peak  | Retention Time (minutes) |
|-------|--------------------------|
| QA-1  | solvent front            |
| QA-2  | 4.6                      |
| QA-3  | 5.6                      |
| QA-4  | 6.4                      |
| QA-5  | 7.2                      |
| QA-6  | 9.2                      |
| QA-7  | 9.6                      |
| QA-8  | 10.6                     |
| QA-9  | 13.0                     |
| QA-10 | 17.2                     |
| QA-11 | 19.0                     |
| QA-12 | 21.2                     |
| QA-13 | 22.6                     |
| QA-14 | 24.0                     |
| QA-15 | 25.6                     |
| QA-16 | 28.6                     |
| QA-17 | 35.2                     |
| QA-18 | 38.2                     |
| QA-19 | 43.6                     |
| QA-20 | 47.6                     |
| QA-21 | 51.6                     |
| QA-22 | 61.0                     |

Fractions containing hemolytic activity, indicative of saponin activity, were rechromatographed by RP-HPLC. immune adjuvant activity was tested by measuring the ability of the purified saponins to enhance the immune response in mice to exogenously administered antigens. The purified saponins demonstrated adjuvant effects at lower doses than the crude extracts. Particularly, the predominant saponins in bark extract (QA-7, QA-17, and QA-18) demonstrated adjuvant activity at doses of 4.5 ug carbohydrate or less (assayed by anthrone). The purified saponins were further characterized by carbohydrate content, reverse phase and normal phase TLC, UV, and infra read spectra.

Milligram quantities of QA-7, QA-17, and QA-18 were purified from Superfos Quil-A by the procedure described below. One g "Quil-A" was suspended in 75 ml methanol and heated at 60° C. for 15 minutes and filtered. The undissolved material was extracted a second time with 50 ml methanol at 60° C. and filtered. The liltrates were evaporated to dryness on the rotaevaporator. A LiChroprep Silica Si 60 column (E.M. Science, 25 mM ID×310 mM L, 40-63 um particle size) was pre-equilibrated in 40 mM acetic acid in chloroform-/methanol/water (62/32/6, v/v/v).

Figure 9A:
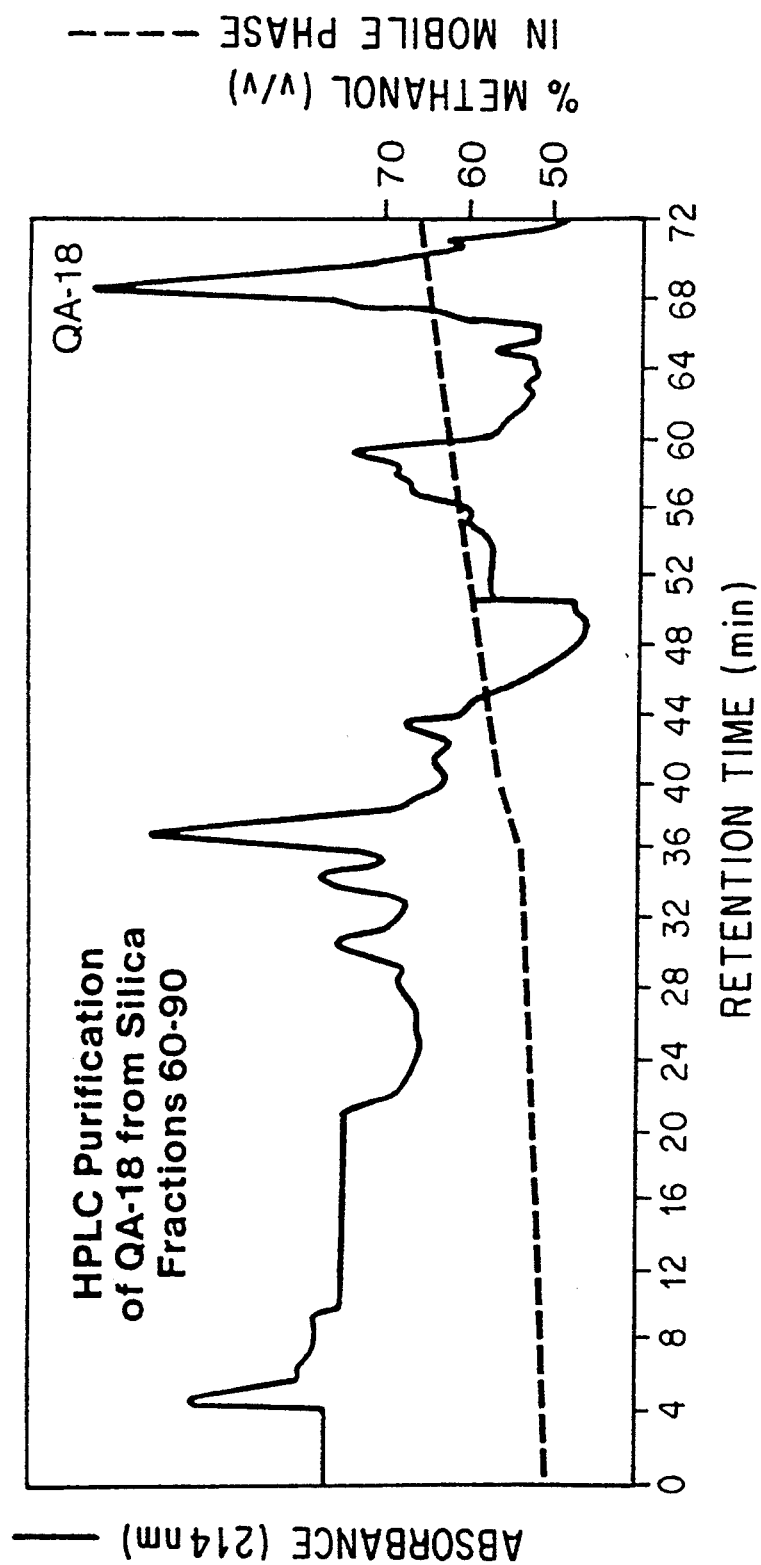
FIGS. 9A–B show the purification of silica fractions of Quillaja saponins by reverse phase HPLC.
Figure 9B:
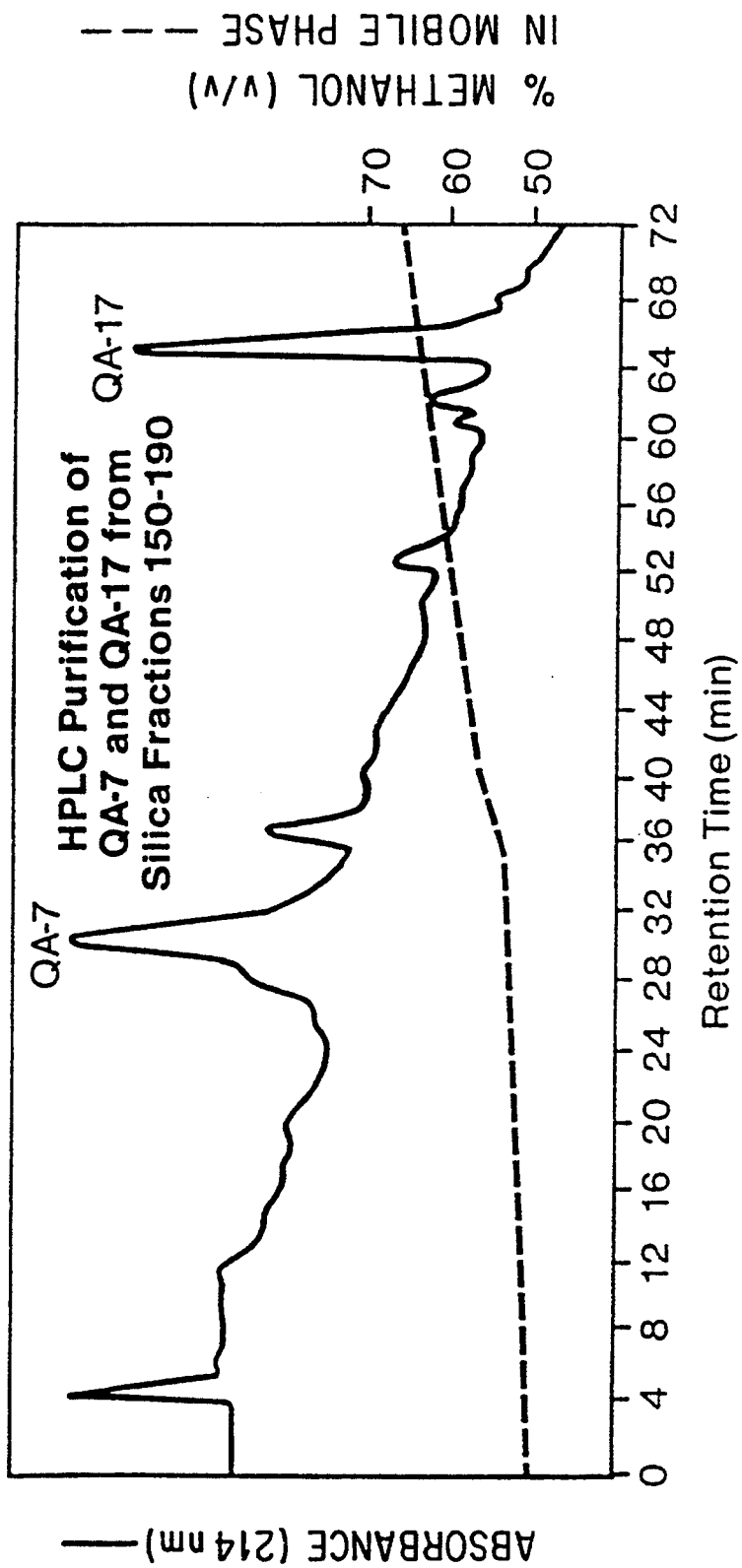

The dried "Quil-A" was dissolved in 5 ml of column solvent and eluted through the silica isocratically in this solvent system at a flow rate of 1 ml/min. Carbohydrate analysis, thin-layer chromatography, and HPLC were used to monitor the fractions for QA-7, QA-17, and QA-18. Fractions 60-90 were greatly enriched in QA-8 and QA-18 whereas 150-190 were enriched in QA-7 and QA-17. These fractions were pooled and flash evaporated prior to further purification by RP-HPLC on Vydac C4 (FIG. 9) using a methanol gradient to elute the pure adjuvants.

EXAMPLE 8

Immunization of Kittens with GP70R

Ten kittens, six to eight weeks of age, were used in the immunization experiments. Prior to immunization, all animals were tested and found to be negative for FeLV antibodies.

The animals were divided into two groups and immunized with either gp70R Preparation I or gp70R Preparation II produced as described in Example 3. Both groups of animals were immunized with 100 ug of the appropriate gp70R preparation emulsified in Freund's complete adjuvant. The animals were immunized parenterally three times at 21-day intervals. Twenty-one days after the last immunization, both groups of animals were challenged with 400 feline sarcoma virus (FeSV) particles per animal.

After each immunization, each animal was measured for antibody levels to FeLV and for levels of neutralizing antibody to FeLV. Fourteen to twenty-one days after challenge with FeSV, in addition to antibody testing, the animals were examined for the presence of virus in serum and formation of tumors. The presence of virus in serum was measured by virus titration (DeNoronha et al., *Journal of the National Cancer Institute* 58:129-130 (1977)), and ELISA using antibody specific for the group antigen (p27) of FeLV which is also common to FeSV. The results of this experiment are shown in Table 1.

Although all nine animals in both groups, who were alive throughout the study, produced antibody to gp70R, only those animals in Group I which were immunized with Preparation I showed any apparent degree of resistance to viral challenge with FeSV. The ability of an animal to produce antibodies capable of neutralizing FeLV correlated directly with the ability of an animal to show resistance to the development of tumors and viremia.

TABLE I

Feline Response to Immunization with gp70R

| Vaccine | Cat | Pre-Challenge Antibody Titer | Tumor Presence | Viral Presence Titer[a] | Viral Presence Elisa | Viral Neutralization[b] 1:2[c] | Viral Neutralization[b] 1:4 |
|---|---|---|---|---|---|---|---|
| PREP I | 11 | 400 | + | 0 | 1+ | 0 | 0 |
|  | 22 | 400 | 0 | 0 | 0 | 50 | 5 |
|  | 24 | 200 | 0 | 0 | 0 | 100 | 99 |
|  | 25 | 800 | 0 | 0 | 0 | 99 | 98 |
|  | 32 | 800 | + | 330 | 3+ | 0 | 0 |
| PREP II | 12 | 1600 | + | 300 | 3+ | 0 | 0 |
|  | 13 | — | DEAD | — | — | — | — |
|  | 21 | 800 | + | 9 | 3+ | 0 | 0 |
|  | 23 | 400 | + | 200 | 3+ | 0 | 0 |
|  | 31 | 800 | + | 100 | 3+ | 0 | 0 |

[a]Foci forming units
[b]in percent
[c]serum dilution

EXAMPLE 9

Immunization with Aluminum Hydroxide-Absorbed GP70R-Delta

Aluminum hydroxide which has been found to have an adjuvant effect for many proteins and is commonly used in vaccines was used as a carrier for gp70R-delta. gp70R-delta prepared by procedure I of Example 6 above absorbs tightly to 10% aluminum hydroxide in the presence of 50 mM Tris-Cl, pH 8.0 containing 6M urea. Approximately 3 ug gp70R-delta were absorbed per 100 ug aluminum hydroxide. The gp70R-delta absorbed to the aluminum hydroxide was washed with phosphate buffered saline (PBS), resuspended in PBS and used for immunization of animals.

CD-1Mice (8–10 weeks old) were immunized intradermally with gp70R-delta absorbed to Al(OH)$_3$ in a total volume of 200 ul PBS in the presence or absence of HPLC-purified saponins QA-17 or QA-18 or a mixture of QA-17 and QA-18. Twenty to Twenty-five ug of gp70R-delta were injected per dose. HPLC-purified saponins QA-17 or QA-18 or a mixture of QA-17 and QA-18 were used at a dry weight dose of 10 ug. Two mice were injected for each formulation. Mice were given a booster injection of gp70R-delta/aluminum hydroxide six weeks after the initial injection. Mouse sera was analyzed for reactivity to FEA, a FeLV subgroup A, at 2, 4, and 8 weeks post-immunization by an ELISA immunoassay. Four weeks following immunization, an anti-FeLV response elicited by the gp70R-delta was observed. HPLC-purified saponin adjuvants QA-17 and QA-18 boosted this response. The response was two orders of magnitude greater at four weeks post-immunization in the presence of QA-17 compared to immunization in the absence of saponin adjuvants. The results of this experiment are shown on FIG. 10.

Anti-FEA IgG was assayed by an ELISA assay. FEA virus (10 ug/ml in PBS) was absorbed to Immulon II plates overnight at 4° C. (100 ul/well). The plates were washed with PBS and nonspecific IgG binding was blocked by incubation for 1 hour with 10% normal goat serum in PBS (100 ul/well) at room temperature. Plates were then washed with 0.05% Tween-20 in distilled water. Sera was diluted in 10% normal goat serum in PBS and incubated for 1 hour at room temperature on the plate at serum dilutions of 10, $10^2$, $10^3$ and $10^4$ (100 ul/well). After washing the plates with 0.05% Tween-20 in distilled water, they were incubated for 30 minutes at room temperature with 100 ul/well of peroxidase-conjugated goat anti-mouse IgG diluted 1/5000 in PBS (Boehringer-Mannheim). After washing the plates with 0.05% Tween-20 in distilled water, the amount of IgG was determined by peroxidase reaction with 3,3′,5,5′-tetramethylbenzidine from the absorbance at 450 nm determined on a Dynatech microtiter plate reader.

EXAMPLE 10

Immunization with Aluminum Hydroxide-Absorbed Gp70R-Delta

CD-1 Mice (8–10 weeks old) were immunized intradermally with 15 ug/dose of alkylated gp70R-delta purified by procedure II of Example 6 (absorbed to aluminum hydroxide as described in Example 6) in 200 ul PBS. HPLC-purified adjuvants QA-7, QA-17, QA-18 and mixtures of the three adjuvants were used at a dry weight dose of 10 ug. Three mice were injected for each formulation. Mouse sera was analyzed by ELISA at 2 and 4 weeks post-immunization for reactivity to FEA as described in Example 9. As with immunization with unmodified gp70R-delta shown in Example 9, immunization with alkylated gp70R-delta elicits an anti-FeLV vital response by four weeks post-immunization. HPLC-purified adjuvants QA-7, QA-17, QA-18 all increase the immune response as compared to immunization in the absence of the saponin adjuvants. QA-17 and mixtures of QA-17 and QA18 -induced the highest response, inducing endpoint titers almost two orders of magnitude greater that immunization in the absence of saponin adjuvants. The results of these experiments are summarized on FIG. 11.

The invention now being fully described, it will be apparent to one of ordinary skill in the art that many changes and modifications can be made thereto without departing from the spirit or scope of the invention as set forth below.

What is claimed as new and is desired to be covered under Letters Patent is:

1. A vaccine capable of protecting a cat against feline leukemia vira (FeLV) comprising an immunogenically effective amount of FeLV subgroup A recombinant gp70 together with a substantially pure saponin adjuvant selected from the group consisting of QA-7, QA-17, QA-18, and QA-21.

2. A vaccine capable of protecting a cat against feline leukemia vira (FeLV) comprising an immunogenically effective amount of FeLV subgroup A recombinant gp70-delta together with a substantially pure saponin adjuvant selected from the group consisting of QA-7, QA-17, QA-18, and QA-21.

3. A vaccine capable of protecting a cat against feline leukemia vira (FeLV) comprising an immunogenically effective amount of FeLV subgroup A recombinant gp90 together with a substantially pure saponin adjuvant selected from the group consisting of QA-7, QA-17, QA-18, and QA-21.

4. The vaccine of any one of claims 1–3, wherein the saponin adjuvant is QA-7.

5. The vaccine of any one of claims 1–3, wherein the saponin adjuvant is QA-17.

6. The vaccine of any one of claims 1–3, wherein the saponin adjuvant is QA-18.

7. The vaccine of any one of claims 1–3, wherein the saponin adjuvant is QA-21.

8. The vaccine of any one of claims 1–3, further comprising aluminum hydroxide.

9. A vaccine capable of protecting a cat against feline leukemia virus (FeLV) comprising an immunogenically effective amount of FeLV subgroup A recombinant gp70-delta together with saponin adjuvant QA-21 and aluminum hydroxide.

* * * * *

UNITED STATES PATENT AND TRADEMARK OFFICE
CERTIFICATE OF CORRECTION

PATENT NO. : 5,352,449
DATED : October 4, 1994
INVENTOR(S) : Beltz et al

It is certified that error appears in the above-indentified patent and that said Letters Patent is hereby corrected as shown below:

In column 16, claim 1, line 37, delete "vira" and substitute therefor, --virus--.

In column 16, claim 2, line 43, delete "vira" and substitute therefor, --virus--.

In column 16, claim 3, line 49, delete "vira" and substitute therefor, --virus--.

Signed and Sealed this

Twenty-first Day of March, 1995

*Attest:*

BRUCE LEHMAN

*Attesting Officer*  *Commissioner of Patents and Trademarks*